(12) United States Patent
Experton et al.

(10) Patent No.: US 11,631,491 B2
(45) Date of Patent: Apr. 18, 2023

(54) PATIENT-FACING MOBILE TECHNOLOGY TO ASSIST PHYSICIAN ACHIEVE QUALITY MEASURES FOR VALUE-BASED PAYMENT

(71) Applicant: HUMETRIX, Del Mar, CA (US)

(72) Inventors: Bettina Experton, Del Mar, CA (US); Christopher Randolph Burrow, Del Mar, CA (US)

(73) Assignee: HUMETRIX, Del Mar, CA (US)

( * ) Notice: Subject to any disclaimer, the term of this patent is extended or adjusted under 35 U.S.C. 154(b) by 0 days.

(21) Appl. No.: 15/898,123

(22) Filed: Feb. 15, 2018

(65) Prior Publication Data

US 2018/0233225 A1 Aug. 16, 2018

Related U.S. Application Data

(60) Provisional application No. 62/597,932, filed on Dec. 12, 2017, provisional application No. 62/459,595, filed on Feb. 15, 2017.

(51) Int. Cl.
*G16H 40/20* (2018.01)
*G16H 20/10* (2018.01)
(Continued)

(52) U.S. Cl.
CPC .......... *G16H 40/20* (2018.01); *G06Q 30/04* (2013.01); *G16H 10/60* (2018.01); *G16H 20/10* (2018.01);
(Continued)

(58) Field of Classification Search
CPC ........ G16H 40/20; G16H 20/30; G16H 40/67; G16H 50/50; G16H 10/60; G16H 50/70;
(Continued)

(56) References Cited

U.S. PATENT DOCUMENTS 6,260,022 B1 * 7/2001 Brown ................ G06F 19/3418
705/2
11,344,235 B2 * 5/2022 Nogueira ........... A61B 5/14532
(Continued)

FOREIGN PATENT DOCUMENTS

KR   10-2014-0039055 A   3/2014
WO      2017/004438 A1   1/2017

OTHER PUBLICATIONS

International Search Report & Written Opinion for counterpart application No. PCT/US18/18428 dated Apr. 25, 2018; 8 pages.
(Continued)

*Primary Examiner* — Michael Tomaszewski
*Assistant Examiner* — Rachael Sojin Stone
(74) *Attorney, Agent, or Firm* — Loza & Loza, LLP; Anthony Smyth

(57) ABSTRACT

Systems and methods for managing healthcare treatment using closed-loop control are described. A method includes wirelessly receiving quality-of-care information from a patient mobile communication device, reporting the quality-of-care information to a quality tracking system, and receiving an incentive payment responsive to reporting the quality-of-care information to the quality tracking system. The quality-of-care information may relate to one or more quality-of-care indicators used to incentivize a provider or consumer of healthcare services. A patient may be alerted to the quality-of-care indicators for specific medical conditions. Personalized and specific notifications generated by an application residing in the patient's mobile device or running in the cloud may be communicated to the patient electronically, including prompts to the patient to take specific action in order to best manage a medical condition or prescribed treatment. A healthcare provider may be noti-
(Continued)

fied of a treatment or quality-of-care recommended action to be taken.

18 Claims, 16 Drawing Sheets

(51) Int. Cl.
| | |
|---|---|
| *G16H 80/00* | (2018.01) |
| *G06Q 30/04* | (2012.01) |
| *G16H 50/50* | (2018.01) |
| *G16H 40/67* | (2018.01) |
| *G16H 50/70* | (2018.01) |
| *G16H 20/60* | (2018.01) |
| *G16H 20/30* | (2018.01) |
| *G16H 10/60* | (2018.01) |

(52) U.S. Cl.
CPC ............ *G16H 20/30* (2018.01); *G16H 20/60* (2018.01); *G16H 40/67* (2018.01); *G16H 50/50* (2018.01); *G16H 50/70* (2018.01); *G16H 80/00* (2018.01)

(58) Field of Classification Search
CPC ........ G16H 20/10; G16H 20/60; G16H 80/00; G06Q 30/04
USPC ............................................................ 705/2
See application file for complete search history.

(56) References Cited

U.S. PATENT DOCUMENTS

| | | | | |
|---|---|---|---|---|
| 11,410,776 | B1* | 8/2022 | Rahman | G16H 50/80 |
| 2002/0010596 | A1* | 1/2002 | Matory | A61B 5/0002 |
| | | | | 705/2 |
| 2005/0256392 | A1* | 11/2005 | Matory | G16H 30/40 |
| | | | | 600/407 |
| 2007/0174092 | A1* | 7/2007 | Lara | G06F 19/3456 |
| | | | | 705/3 |
| 2009/0094058 | A1* | 4/2009 | Reiner | G06F 19/3456 |
| | | | | 705/3 |
| 2010/0241465 | A1* | 9/2010 | Amigo | G06Q 40/08 |
| | | | | 705/4 |
| 2011/0029030 | A1* | 2/2011 | Yun | A61K 31/4168 |
| | | | | 607/3 |
| 2011/0288380 | A1 | 11/2011 | Inciardi et al. | |
| 2013/0013331 | A1* | 1/2013 | Horseman | A61B 5/0022 |
| | | | | 705/2 |
| 2013/0142367 | A1* | 6/2013 | Berry | G16H 40/40 |
| | | | | 381/315 |
| 2013/0280682 | A1* | 10/2013 | Levine | G09B 25/00 |
| | | | | 434/236 |
| 2014/0108044 | A1* | 4/2014 | Reddy | G16H 15/00 |
| | | | | 705/3 |
| 2014/0164003 | A1* | 6/2014 | Thesman | G06Q 50/22 |
| | | | | 705/2 |
| 2014/0247137 | A1* | 9/2014 | Proud | G06K 19/07762 |
| | | | | 340/870.01 |
| 2014/0278468 | A1 | 9/2014 | Mayer et al. | |
| 2015/0112703 | A1 | 4/2015 | Sysko et al. | |
| 2016/0038675 | A1* | 2/2016 | Estes | A61M 5/1413 |
| | | | | 604/151 |
| 2017/0199985 | A1* | 7/2017 | Mazlish | A61M 5/14244 |
| 2017/0215068 | A1* | 7/2017 | Modzelewski | H04L 63/0492 |
| 2020/0170513 | A1* | 6/2020 | Walker | G16H 15/00 |
| 2021/0345952 | A1* | 11/2021 | Harris | A61M 15/009 |

OTHER PUBLICATIONS

EP Appln. No. 18754343. Supplementary Search Report (dated Oct. 26, 2020).

Korean Patent Application No. 10-2019-7024974. Office Action (dated Aug. 25, 2022).

* cited by examiner

PATIENT-FACING MOBILE TECHNOLOGY TO ASSIST PHYSICIAN ACHIEVE QUALITY MEASURES FOR VALUE-BASED PAYMENT

PRIORITY CLAIM

This application claims priority to and the benefit of provisional patent application No. 62/459,595 filed in the United States Patent Office on Feb. 15, 2017, and of provisional patent application No. 62/597,932 filed in the United States Patent Office on Dec. 12, 2017 the entire content of these applications is incorporated herein by reference as if fully set forth below in its entirety and for all applicable purposes.

TECHNICAL FIELD

The present invention relates generally to patient use of mobile computing devices generating personalized healthcare notifications for patient users to assist their physicians meet specific quality-of-care indicators and receive incentive value-based payments.

BACKGROUND

With the ongoing rising cost of healthcare around the world, public and private healthcare payers are moving away from fee-for-service healthcare to value-based payment models. With these new healthcare models, physicians and healthcare organizations are no longer paid for the volume of services they provide, with the risk of ordering unnecessary tests and procedures, but for the value or quality of the care they provide to their patients. In the United States, the federal government has defined new policy and regulatory measures to govern value-based payment for its Medicare program beneficiaries such as with Accountable Care Organizations (ACOs), with the Medicare Access and CHIP Reauthorization Act (MACRA) and for the general public with the 21st Century Cures Act. In the United Kingdom, the National Health Services (NETS) is using the Quality Outcomes Framework (QOF) to reward General Practitioners (GPs) with annual incentive payments when they meet and report on specific quality measures. A similar system called ROSP (Remuneration sur Objectives de Sante Publique) is used in France to reward general practitioners with end of year incentive payments when they meet defined quality-of-care criteria.

Many of the quality indicators driving incentive payments to healthcare providers relate to the care of patients with chronic medical conditions. Treatment for these chronic medical conditions not only take place in the clinic, but also outside the clinic and in the home of these patients during their daily life. To best manage their chronic conditions, patients need to not only comply with or adhere to the treatment prescribed by their physicians, but also manage their healthcare across different providers and various lifestyle factors related to their conditions regularly overtime. In order to meet defined quality-of-care indicators when providing medical care to their patients, physicians therefore depend on their patients' compliance to treatment and on an effective and close communication with their patients to proper diagnose, and monitor treatment progress and its efficacy. To optimally achieve and report on these quality indicators to receive these incentive payments, healthcare providers are using Healthcare Information Technology (HIT) systems such as electronic medical record systems (EMRs) to guide them along the quality-of-care reporting process. However, most of the time these EMRs fail to include patient generated information with regards to the patients' compliance to treatment, treatment progress, and other patient generated data indicative of the efficacy and quality-of-care the patient have received. This is again particularly true for patients suffering for chronic conditions, whose quality-of-care depends on treatment adherence, lifestyle modifications, and regular self-care at home overtime.

SUMMARY

Certain aspects disclosed herein can improve information flow between providers, patients and payers to ensure cost-effective and better targeted treatment for healthcare recipients.

In various aspects of the disclosure, a method for managing electronic medical records includes authenticating the identity of a user of a patient mobile communication device during an interaction between the user of the patient mobile communication device and a healthcare provider, receiving information through a wireless communication interface that authenticates an identity of the provider, collating electronic healthcare records associated with the user of the patient mobile communication device from a plurality of sources, transferring information including a portion of the electronic healthcare records to the provider device responsive to receiving the information that authenticates the identity of the patient, recording information characterizing the transfer of information to the provider device in patient metadata maintained by the patient mobile communication device, and transmitting the patient metadata to a rewards server. The rewards server may be configured to calculate a financial benefit to the user based on one or more transfers of electronic healthcare records to or from the healthcare provider.

In one aspect, the method includes receiving one or more updates to the electronic healthcare records associated with the user of the patient mobile communication device, and transmitting updated electronic healthcare records to at least one of the plurality of sources. The rewards server may be configured to calculate the financial benefit to the user based on transmission of the updated electronic healthcare records. The method may include decoding the updated electronic healthcare records to identify one or more procedures performed by the healthcare provider, and recording the one or more procedures in the patient metadata. Decoding the updated electronic healthcare records may include decoding an international or national standardized health data code list for medications, diagnoses, laboratory tests, providers, procedures, immunizations, or individual medical professions.

In one aspect, the method includes using a GPS location service to automatically obtain a geographical location associated with the interaction between the user of the patient mobile communication device and the healthcare provider, and recording the geographical location in the patient metadata.

In various aspects, a method for managing healthcare services includes receiving patient metadata related to an interaction between a patient and a healthcare provider where the patient metadata is generated by a mobile communication device operated by the patient, determining from the patient metadata that electronic healthcare records associated with the patient were transferred to or from the healthcare provider during the interaction between the patient and the healthcare provider, and calculating a financial benefit to the user based on the transfer of the electronic healthcare records.

In one aspects, the patient metadata identifies that one or more updates to the electronic healthcare records were transmitted to the mobile communication device operated by the patient. The method may include calculating a financial benefit to the user based on the transfer of the one or more updates. The method may include decoding the patient metadata to identify one or more procedures performed by the healthcare provider, and identifying the one or more procedures to a healthcare billing system. Decoding the updated electronic healthcare records may include decoding an international or national standardized health data code list for medications, diagnoses, providers, laboratory tests, procedures, immunizations, or individual medical professions.

In one aspect, the method includes receiving provider metadata related to the interaction between the patient and the healthcare provider where the provider metadata is generated by a computing device operated by the healthcare provider, and calculating a financial benefit to the healthcare provider when the provider metadata records the transfer of electronic healthcare records. The provider metadata may identify that one or more updates to the electronic healthcare records were transmitted by the healthcare provider to the mobile communication device operated by the patient. The method may include calculating a financial benefit to the healthcare provider based on the transfer of the one or more updates. The method may include generating a characterization of the interaction between the patient and the healthcare provider based on correspondences between the patient metadata and the provider metadata, and providing the characterization of the interaction to a healthcare billing system.

DETAILED DESCRIPTION

Figure 1:
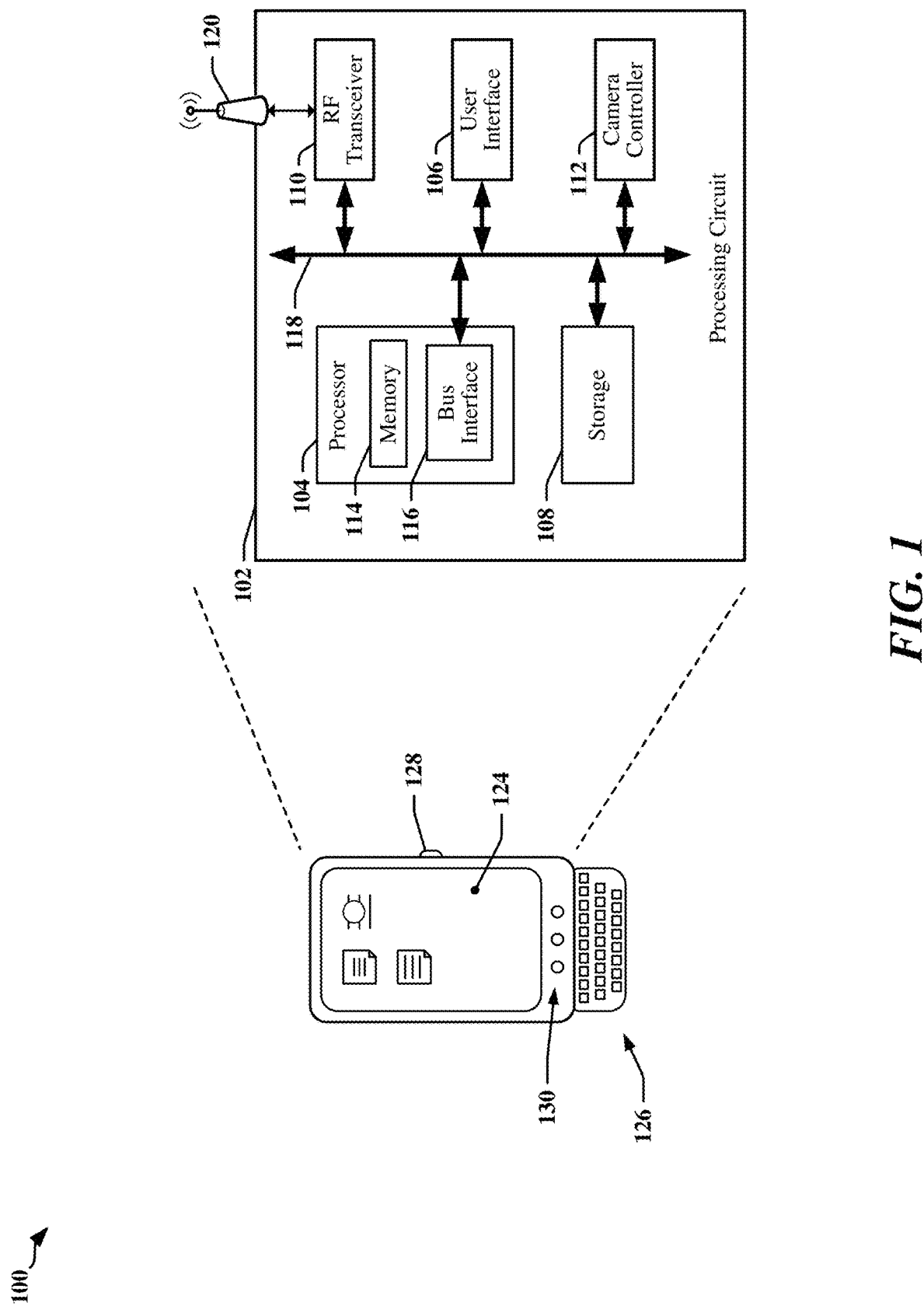
FIG. 1 illustrates an example of a hardware implementation for an apparatus employing a processing system.

The detailed description set forth below in connection with the appended drawings is intended as a description of various configurations and is not intended to represent the only configurations in which the concepts described herein may be practiced. The detailed description includes specific details for the purpose of providing a thorough understanding of various concepts. However, it will be apparent to those skilled in the art that these concepts may be practiced without these specific details. In some instances, well known structures and components are shown in block diagram form in order to avoid obscuring such concepts.

Several aspects of records management systems will now be presented with reference to various apparatus and methods. These apparatus and methods will be described in the following detailed description and illustrated in the accompanying drawing by various blocks, modules, components, circuits, steps, processes, algorithms, etc. (collectively referred to as "elements"). These elements may be implemented using electronic hardware, computer software, or any combination thereof. Whether such elements are implemented as hardware or software depends upon the particular application and design constraints imposed on the overall system.

By way of example, an element, or any portion of an element, or any combination of elements may be implemented with a "processing system" that includes one or more processors. Examples of processors include microprocessors, microcontrollers, digital signal processors (DSPs), field programmable gate arrays (FPGAs), programmable logic devices (PLDs), state machines, gated logic, discrete hardware circuits, and other suitable hardware configured to perform the various functionality described throughout this disclosure. One or more processors in the processing system may execute software. Software shall be construed broadly to mean instructions, instruction sets, code, code segments, program code, programs, subprograms, software modules, applications, software applications, software packages, routines, subroutines, objects, executables, threads of execution, procedures, functions, etc., whether referred to as software, firmware, middleware, microcode, hardware description language, or otherwise. The software may reside on a computer-readable medium. A computer-readable medium may include, by way of example, a magnetic storage device (e.g., hard disk, floppy disk, magnetic strip), an optical disk (e.g., compact disk (CD), digital versatile disk (DVD)), a smart card, a flash memory device (e.g., card, stick, key drive), Near Field Communications (NFC) token, random access memory (RAM), read only memory (ROM), programmable ROM (PROM), erasable PROM (EPROM), electrically erasable PROM (EEPROM), a register, a removable disk, a carrier wave, a transmission line, and any other suitable medium for storing or transmitting software. The computer-readable medium may be resident in the processing system, external to the processing system, or distributed across multiple entities including the processing system. Computer-readable medium may be embodied in a computer-program product. By way of example, a computer-program product may include a computer-readable medium in packaging materials. Those skilled in the art will recognize how best to implement the described functionality presented throughout this disclosure depending on the particular application and the overall design constraints imposed on the overall system.

Overview

Certain aspects of the present disclosure relate to a control system that may implemented to improve the effectiveness of treatments prescribed by healthcare providers. The control system may respond to changing circumstances by adjusting and/or modifying a treatment plan. In some instances, the patient for whom the treatment is prescribed may be recalled for consultation based on trends, conditions or alerts generated by the control system.

According to certain aspects disclosed herein, treatment prescribed by a healthcare provider may include a treatment plan distributed to one or more mobile processing devices operated by the patient. The mobile processing devices may include a communication device operated or associated with the patient, such as a smartphone, smart watch and/or a wearable processing device. The mobile processing device may monitor medical sensors and/or may gather information input by the patient or automatically generated information such as location and activity of the patient. The mobile processing device may provide sensor information and other information as feedback to the control system. In one example, the mobile processing device may alert and remind the patient to execute elements of the treatment plan according to a defined schedule and may provide confirmation of completion of tasks as feedback to the control system.

In certain aspects, patients and healthcare providers may be incentivized to communicate activities to the control system. Methods, apparatus, and computer program products are disclosed that can alert patients with personalized and specific notifications related to the quality-of-care for specific medical conditions to be communicated to their physicians for them to best meet and report payer defined quality-of-care indicators in order for them to receive value-based incentive payments. The personalized and specific notifications are generated by a computer program located in the patient's mobile device or running in the cloud and communicated to the patient via his mobile device or virtual assistants. The computer program generating these periodic notifications uses algorithmic computations of the user's personal health information, including personal diagnoses, medications, and other individual treatment data which are either self-entered or retrieved from the patient's electronic health record(s), and collected via the user's personal mobile devices with clinical guidelines or best practice criteria relating to the quality-of-care indicators healthcare providers have to meet and report on to receive their incentive payments. Notifications received by the patient may be specific to the quality-of-care indicator and prompt the patient to both take a specific action to best manage his medical condition or prescribed treatment, and communicate with his healthcare provider when his specific treatment or treatment goal has taken place or has been achieved, so that his healthcare provider can report to the payer organization issuing the earned incentive payments that the specific quality-of-care criteria or outcome has been met.

A method, an apparatus, and a computer program product are disclosed that can alert patients with personalized and specific notifications related to the quality-of-care for specific medical conditions to be communicated to physicians. The notifications may relate to actions required by the physician to meet and report payer-defined quality-of-care indicators in order for the physicians to receive value-based incentive payments. Personalized and specific notifications generated by software, applications or other circuit or module located in the patient's mobile device or executed in a computing cloud may be communicated to the patient electronically. The specific notifications may be communicated through the patient's mobile device. Specific notifications may relate to one or more quality-of-care indicators and may be provided to prompt the patient to take a specific action to best manage a medical condition or prescribed treatment, and communicate with a healthcare provider the quality-of-care recommended action to take, to confirm that such action has been taken, and/or to communicate with the physician when the specific treatment or treatment goal has taken place or has been achieved, such that the healthcare provider can report on recommended quality-of-care action, quality-of-care action taken by the physician, and/or achievement of specific quality-of-care criteria or outcomes required to obtain earned incentive payments.

Example of an Apparatus

FIG. 1 illustrates an example of an apparatus (here a mobile device 100) that may be adapted in accordance with certain aspects disclosed herein. The mobile device 100 may include a processing circuit 102 comprising one or more integrated circuit (IC) devices 104, 106, 108, 110, and/or 112. The mobile device 100 may provide a display 124 and user input devices 126, 128, 130. The processing circuit 102 may be implemented with a bus architecture, represented generally by the bus 118. The bus 118 may include any number of interconnecting buses and bridges depending on the specific application of the processing circuit 102 and the overall design constraints. The bus 118 links together various circuits and/or devices 104, 106, 108, 110, and/or 112, including one or more processors, represented generally by the processing device 104, a user-interface support module or circuit 106, computer-readable storage media, represented generally by the storage device 108, one or more communication interfaces, represented generally by the radio frequency (RF) transceiver 110, and an imaging interface, represented generally by the camera device 112. The bus 118 may also link various other circuits such as timing sources, peripherals, voltage regulators, and power management circuits, which are well known in the art, and therefore, will not be described any further. The processing circuit 102 may include a bus interface 116 that provides an interface between the bus 118 and the processing circuit 102. In some instances, the bus interface 116 controls and provides access between multiple devices 104, 106, 108, 110, and/or 112. In some embodiments, bus interface 116 may be an integral part of the processing circuit 102. In some embodiments, the bus interface 116 may interface a processing system with standards-defined bus, such as a universal serial bus (USB), or the like, that permits external peripherals to be coupled to the mobile device 100.

An RF transceiver 110 or other transceiver may provide a means for communicating with various other apparatus over a transmission medium. Another type of transceiver may be employed to provide a proprietary wired interface or a wired interface compliant or consistent with a standard such as universal serial bus (USB), FireWire, Ethernet, Serial Advanced Technology Attachment (SATA), etc. The RF transceiver 110 may provide a wireless interface and transmit and receive radio signals through an antenna 120 using a proprietary or standardized signaling protocol such as IEEE 802.11, WiFi, WiMax, CDMA, WCDMA, Bluetooth, etc. In one example, the RF transceiver 110 and an antenna 120 may enable the mobile device 100 to communicate as a radio frequency identification device (RFID) device. Other transceivers may enable optical, infrared and other communications. Depending upon the nature of the apparatus, a user interface support module or circuit 106 (e.g., keypad, display, speaker, microphone, joystick) may also be provided.

The processing device 104 is responsible for managing the bus 118 and general processing, including the execution of software stored on the computer-readable medium 108. The software, when executed by the processing device 104, causes the processing circuit 102 to perform the various functions described infra for any particular apparatus. The computer-readable medium 108 may also be used for storing data that is manipulated by the processing device 104 when executing software.

Electronic Records Including Electronic Health and Insurance Claim Records

The various concepts presented throughout this disclosure may be implemented using a device that is configured to interface and/or interact with broad variety of telecommunication systems, network architectures, and communication standards.

Various aspects of the present disclosure relate to an example involving electronic health records, which may include records found in healthcare provider EMR systems or in insurance claims systems. The scope of the invention is not limited to electronic health records and various aspects of the invention may relate to the management and access of other types of records, including legal records, financial records, employment records, and so on. For example, certain aspects of the invention are applicable to point-of-sale authorization and identification of the parties to a transaction. In another example, certain aspects of the invention may enable secure transactions and exchange of information between clients and financial institutions. For simplicity of description, however, examples involving electronic health records are used throughout this disclosure.

In the example of electronic health records, portable computing devices may be used to authenticate a patient and/or a healthcare provider to enable and/or authorize and exchange of the electronic health records. The patient may elect to push electronic healthcare records to the healthcare provider. The healthcare provider may elect to push updates and/or new records to the patient. Healthcare records may also include images, such as radiographic images initially captured through the use of radiography, magnetic resonance imaging (MRI), computerized tomography (CT-Scan or CATSCAN), ultrasonic imaging, or other imaging processes. Records and updates may be pushed over local networks using a Bluetooth connection, a wireless network or by optical exchange of information that provides a communication path that can be separate and distinct from the networking path used to deliver records. In one example, a quick response code (QRC) may be presented to a healthcare provider, whereby the QRC includes information that can be used to identify a network location of the records, cryptographic keys necessary to decrypt the records once retrieved from the network location, and other information.

The portable computing devices may directly deliver the portion of the information electronically using a Bluetooth connection, a wireless network or by an intermediate network server, or by any other method of electronic or wireless communication. Exchange of records and other information between the patient and the provider may be effected using multiple communications channels or links. In one example, a first channel may provide information that includes a network address of the records and corresponding cryptographic keys necessary to extract the records, while a second channel may be used to deliver the encrypted records and/or cryptographic keys. The first channel may be implemented using a camera or optical scanner to read an encoded optical image, such as a QRC or another barcode.

According to certain aspects disclosed herein, a patient may be incentivized to provide medical information to a healthcare provider and/or a payer. The exchange of medical records facilitated through a mobile computing device such as a smartphone or wearable device can be preconditioned on authorization provided by the subject and/or owner of the medical records. A patient may provide authorization for medical record transfer through a smartphone or another device after the patient is identified and authenticated to be the user of the smartphone or another device. In some embodiments, the smartphone or other device may be adapted to transmit information (which may be referred to as health records metadata) regarding a medical record exchange to reward system in order to reward the patient for exchanging the medical record. In some examples, the patient may provide authorization to transmit the health records metadata to the reward system when enrolling in a rewards plan. The health records metadata may be used to confirm presence at a healthcare provider facility, provision of current and complete healthcare records to a provider, and billing related information.

The reward system may provide discounts, rebates and other valuable benefits to an enrollee. An incentivized patient may be more willing to provide a health records through a personal mobile computing device in order to receive the rewards. The healthcare provider receiving updated healthcare records may more efficiently and effectively treat the patient, and the payer may benefit from elimination of duplicative or unneeded procedures.

Examples of Networks Configured to Transfer Electronic Health Records

Figure 2:
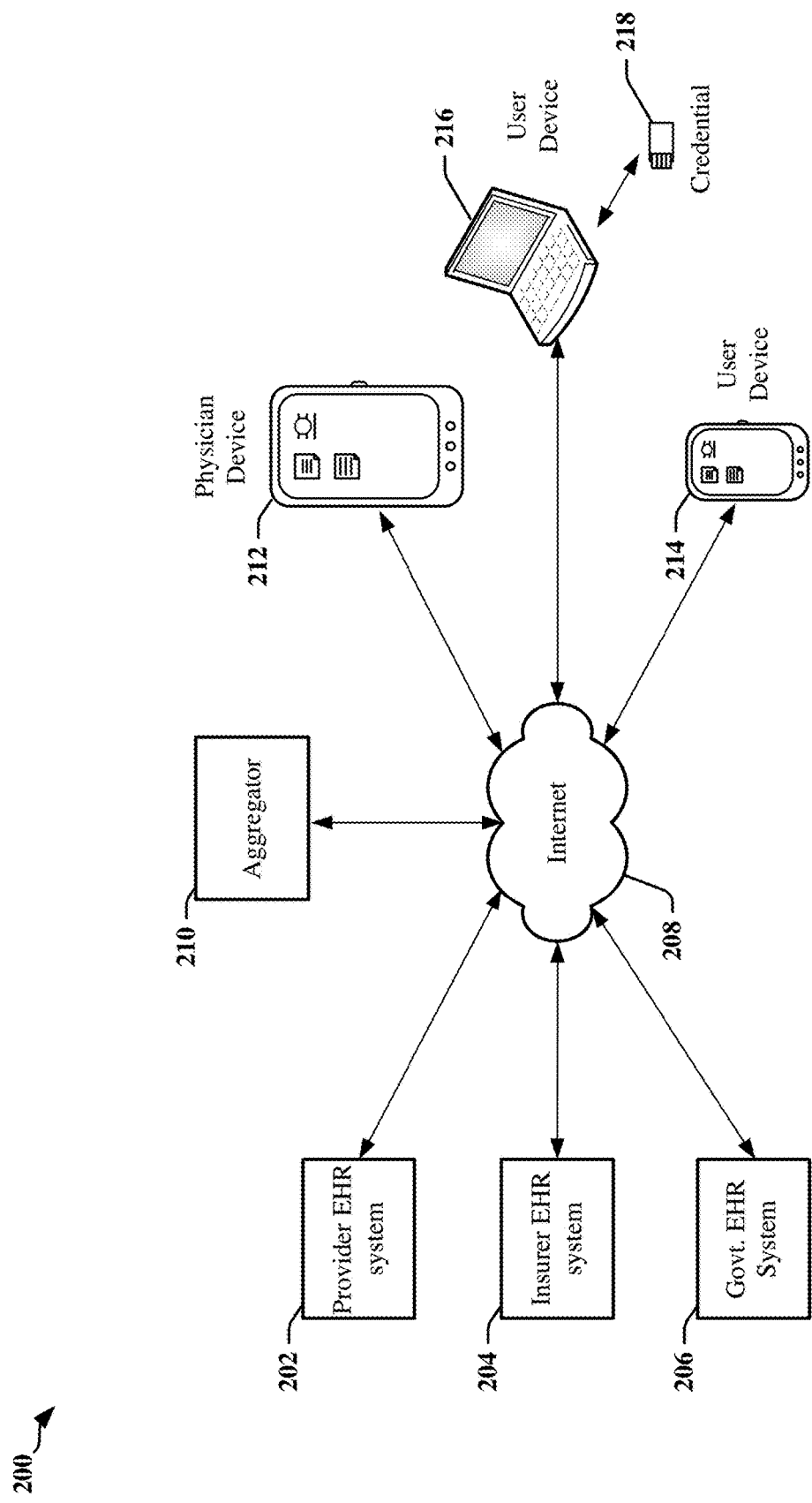
FIG. 2 illustrates an example of an electronic records delivery system according to certain aspects described herein.

FIG. 2 illustrates a simplified example of a system 200 adapted according to certain aspects of the invention. Electronic Health Records (EHRs) may be maintained in various physical locations and/or on EHR systems 202, 204, and 206 operated by a plurality of different parties including healthcare provider EHR systems 202, payer EHR or Claims systems such as those used by insurers and/or EHR systems 206 operated by government entities. In one example, records maintained on EHR systems 202, 204, and 206 may include duplicate information maintained in two or more of the EHR systems 202, 204, and 206. In other examples, at least some EHR information may be aggregated, accumulated, and/or maintained in a single EHR system 202, 204 or 206.

A user may access records through a client device 214 or 216, such as a smart phone, a tablet computing device, a notebook computer, a wearable computing device, a smart watch, a health or fitness tracker, eyewear, or other suitable mobile device. In some instances, the user may access records through an appliance that incorporates or is controlled by a computing system or other processing device. The user may be a service provider. The user may be an individual record owner who may be a client or patient of a provider system and/or a client or an individual insured by an insurer, or an agent of the record owner. In certain circumstances, the user may be an emergency responder acting on behalf of a debilitated, injured or otherwise incapacitated individual record owner. In many instances, the record owner is a patient who receives healthcare services in multiple locations and/or from multiple healthcare providers. Healthcare providers may include one or more of a primary care provider (physician), a physician specialist, an emergency responder and a pharmacy. The patient may be insured by a private or public health insurance plan. Each of these different healthcare entities may maintain separate and distinct electronic health records for the patient.

A client device 214, 216 may be adapted or configured to enable access to personal electronic health records. In some examples, an application or agent may be installed and/or downloaded to the client device 214, 216 to enable access to personal electronic health records that are maintained on one or more centralized databases corresponding to the EHR systems 202, 204 and 206. The user may access electronic health records related to a transaction or the provision of healthcare services to a patient, and the records accessed may comprise personal health records, such as medical records and insurance records, which may be remotely located on centralized databases embodied in EHR systems 202, 204, and 206 operated by a service provider, insurer or other entity.

In one example, databases maintained by one or more EHR systems 202, 204, and 206 may be accessed through a network 208. The network 208 may be implemented using a wireless network, a cellular access network, the Internet and/or one or more private network, etc. In certain embodiments, a record owner can access EHR systems or databases individually to retrieve records related to a specific activity, service, and/or provider. In some embodiments, the record owner may identify a set of EHR systems or databases to be accessed and aggregated, combined, collated, or merged to obtain a combined set of EHRs and/or a report identifying relevant or available EHRs. In some embodiments, the record user can specify a type of record to be accessed, regardless of which EHR systems or databases maintain such records or types of records. In some embodiments, a record owner can generate a combined individual record for immediate access and use by the user, or for delivery to a healthcare provider such as a physician. Records may be delivered to the physician through the physician's personal computing device or a computing device owned or operated by a healthcare provider (e.g., the physician device 212). The record owner may produce a combined record on-demand (on-the-fly), or may provide access to a combined individual record that is maintained by, or on behalf of the record owner and which is updated automatically and/or periodically. In some embodiments, the record owner may authorize and/or enable a provider to access EHRs from a single source, from multiple sources, and/or from an aggregator 210. In some embodiments, a record owner may authorize and/or enable a provider to access certain types of records, regardless of the location of those records. Other configurations of components, functions and modules may be implemented. For example, the aggregator 210 may be implemented in a client device 214, 216.

In the example illustrated in FIG. 2, the individual records may be delivered to a physician device 212, such as a tablet computer or smart phone, although the combined individual record may also be delivered to a server or other computer of an EHR system 202, 204 or 206. In some embodiments, the record owner may cause a server or other network device (e.g., an aggregator 210) to deliver the combined individual record sourced from one or more EHR systems 202, 204, or 206 to a physician device 212 or other computing device, such as a desktop computer. In one example, the aggregator 210 may be used to provide individual records when a record owner does not have access to a client device 214 capable of producing and delivering the individual record or when the record owner's device (client device 214, 216, 218) cannot connect to the physician device 212 or EHR systems 202, 204, or 206.

Identification and authentication information may be maintained on a client device 214, 216 to permit the record owner to access each of EHR systems 202, 204, and 206. The maintenance and control of the identification and authentication information by the record owner can reduce overall system complexity because a single command and identification process at the record owner's device (e.g., client device 214 or 216) can initiate automatic access to relevant records on the EHR systems 202, 204, 206 and/or to relevant records provided by an aggregator 210. For example, an agent installed on the client device 214, 216 may be configured to identify and authenticate the user of the client device 214, 216 through password, challenge words, a biometric scan and/or other means of authentication known in the art. In some examples, authentication may be confirmed by a trusted third-party device or service provider. Authentication information may be provided to each of the EHR systems 202, 204, and 206 and/or the aggregator 210 to enable access to the EHR information related to the record owner. In one example, the client device 214, 216 of the record owner may supply the authentication information. In another example, the trusted third-party device or service provider may provide the authentication information.

The process of authentication and/or point of origin of the request may be recorded and may be used to prove consent of a record holder to a transfer of records to a provider. In some embodiments, a request from a user to transfer records may be considered or configured to include consent of the record owner, based on prior identification and/or authentication of the identity of the user as the record holder. The record owner may be presented with a request to confirm a transfer request. The request for confirmation may include a request for identification and/or a request to authenticate the identity of the recipient of the transfer request. In some embodiments, the user may configure the type of transfer to be performed for each request. For example, consent may be limited to a subset of the owner's EHR record. In some embodiments, the record owner may configure a default specification of the types of record that can be transferred to one or more service providers. Authenticated requests to transfer information and acknowledgements of such requests, as well as acknowledgements of delivery and/or acceptance of a requested EHR may be logged at the client device 214 or 216, the physician device 212, a physician management system, one of the record holder's EHR systems 202, 204, 206, and/or an aggregator 210. The user may authorize and/or initiate an access to EHRs through the facilities of a service provider.

The user may prepare a combined EHR report or may store a set of EHR information from a variety of sources on a mobile device or on a storage device. Locally maintained information is typically encrypted. The record holder may transfer a portion or all of locally maintained information to a healthcare provider when seeking healthcare services. The user may also access certain records on-line from home to check on his insurance status, medical appointments, to see prescription refill status or to communicate by e-mail with his physicians.

Certain embodiments provide an interface to multiple electronic health records for both users and service providers. A user may provide authorization that enables a service provider to access some or all of the user's combined records. A first provider may, at the user's discretion, access the user's individual EHRs maintained by a second provider where the second provider may be physically located at a different healthcare facility. In one example, a physician may directly and easily access all of the user records necessary to obtain a current view of the user's complete medical history, insurance eligibility status, and other information. Moreover, medical practitioners can directly access the user's records in order to update the user's health information.

When transferring records, user identification information may be authenticated using any combination of a user ID, password, challenge question and biometric information. Typically, the transfer is made contingent upon a two-way identification of a record holder and a healthcare provider. In-person identification may be made using direct sight. Additionally, both parties' portable devices may establish a connection that is confirmed by both the record holder and the healthcare provider. In one example, the connection may comprise a session secured using encryption keys that are exchanged between the users. The encryption keys may be used to encrypt and decrypt information transmitted between the devices of the users. In some embodiments, the transfer may be restricted to proximately located devices. In one example, the record holder may initiate contact by selecting a physician's tablet computer from a list of devices within Bluetooth range, or within the same WiFi domain. The physician typically accepts the connection before the transfer is initiated.

In certain embodiments, records may not be exchanged without first obtaining a positive identification of the recipient. When the record holder and the healthcare provider are located in different physical locations, information identifying a physical location may be provided by one or more of the record holder and the healthcare provider. The identification of a physical location may be made using a global positioning system, location information provided by a wireless network and from other sources, including triangulation by a cellular network. For example, certain wireless network telecommunications services can provide accurate positional information based on triangulation and/or certain signaling characteristics of mobile devices. In some embodiments, an authentication service may be used to verify identity of a record holder and a healthcare provider, and the record holder and the healthcare provider may be connected when the authentication service confirms identity of the parties, even when the parties are located in different physical locations.

In certain embodiments, user devices of a record holder and a healthcare provider may be incompatible and may not be capable of direct connection. For example, an Android-based device may not be able to connect securely with a tablet computer that operates using a different operating system. When incompatible devices are used, a gateway may be employed to facilitate the connection of the devices. The gateway may provide extended handshake services that identify both devices and establish a secure link between the devices. The gateway may be provided using a local or network server and/or a cloud service.

In certain embodiments, global positioning technology may be used to confirm specific locations and/or proximity of the record holder and provider devices. In some embodiments, radio access technologies such as fourth generation long term evolution (4G LTE) and fifth generation (5G) radio access technologies may include location services that can be used to determine proximity or physical location information.

General purpose computing devices 216, such as a notebook or desktop computer, may also be used to access medical records, even where the computing device 216 does not belong to the record owner. Record owner may provide an electronic credential 218 that, when read and used by computing device 216, enables automatic access of combined individual records. Electronic credential 218 may comprise a hand-held device with a non-transitory memory and an embedded microprocessor or other programmable device. The electronic credentials may comprise a smart card, a USB flash drive, and radio-frequency identification (RFID) device, a Near Field Communication (NFC) token, web-enabled phones, etc. The electronic credentials may be embodied in an identification card or other format easily stored and secured by the user.

In certain embodiments, access to the user's EHR information may be obtained by presenting the electronic credential 218 to a computing device (e.g., the client device 214 or 216), whereby the computing device can establish a wired or wireless connection with the electronic credential 218 that enables an exchange of data. The electronic credential 218 may comprise a small portable device issued by an insurer, a government agency, a primary healthcare provider system, etc. The electronic credential 218 may comprise a memory that maintains information including a personal identifier, a unique identifier assigned to the individual, an EHR locator address, login information, and/or other identifying information. The user may use the electronic credential 218 to access one or more EHR systems 202, 204, and 206 through a client device 214 or 216, such as a personal computer (PC), tablet computer, smart phone, wearable computing device (e.g., a smart watch, a health or fitness tracker, eyewear, etc.), or other suitably equipped processing device. In one example, the electronic credential 218 comprises a flash drive, a smart card, or a device that can connect wirelessly to the client device 214 or 216. The user may present the electronic credential 218 to the client device 214 or 216 in a manner appropriate to allow the electronic credential 218 to exchange information with the client device 214 or 216, whereby the client device 214 or 216 may automatically access and login to one or more EHR systems 202, 204, and 206 using the record owner's identification. The user may have access to the EHR systems 202, 204, and 206 for automated and simultaneous real-time access to medical records maintained therein. In one example, an agent or other application software embedded in the electronic credential 218, or accessed through a network 208 using information stored on the electronic credential 218, may be downloaded to the client device 214 or 216 to enable harvesting of selected data from the different EHR systems 202, 204, and 206 and generate an on-the-fly summary record for a physician to view and use.

Certain embodiments enable automated access to multiple data sources. In one example, an electronic credential 218 comprises an encrypted "electronic keychain" that may be maintained as a knowledgebase that comprises identification and lists of sources of health-related information for an individual. The knowledgebase can include both the Internet address as well as identification and other credentials needed to enable access to the data. Typically, the health information is maintained by a plurality of healthcare providers or practitioners, and information may be accessible through repositories or databases, including insurance databases and healthcare record portals.

An electronic credential 218 may comprise a device that includes a combination of hardware and software that can encrypt and decrypt information stored on the electronic credential 218. The electronic credential 218 may be embodied in intelligent electronic devices (e.g., devices having at least a programmable controller), such as a universal serial device, a smart phone, a wearable computing device, a smart watch, a health or fitness tracker, eyewear, a PC and a tablet computer. The electronic device may have sufficient processing capacity and storage to operate as a self-contained EHR access portal.

In certain embodiments, an on-the-fly summary of health information can be provided at a medical provider facility, or other location. Information provided by an electronic keychain may be used to initiate access and retrieval of information sourced from multiple EHR systems 202, 204, and 206. Information provided by the electronic keychain may include one or more agents or applications that may compile multiple electronic health records into a single summary form. The summary form may be provided in a standardized format, such as continuity of care record ("CCR"), a continuity of care document ("CCD") in various standardized formats including HL7 FHIR resources, and other suitable formats. In some embodiments, compiled health records may be presented in a consistent summary format regardless of the format used by the originating source. Accordingly, information provided or accessed through the electronic keychain may include templates and conversion modules that can be used to filter and reformat EHR information sourced from a variety of EHR systems 202, 204, and 206.

Figure 3:
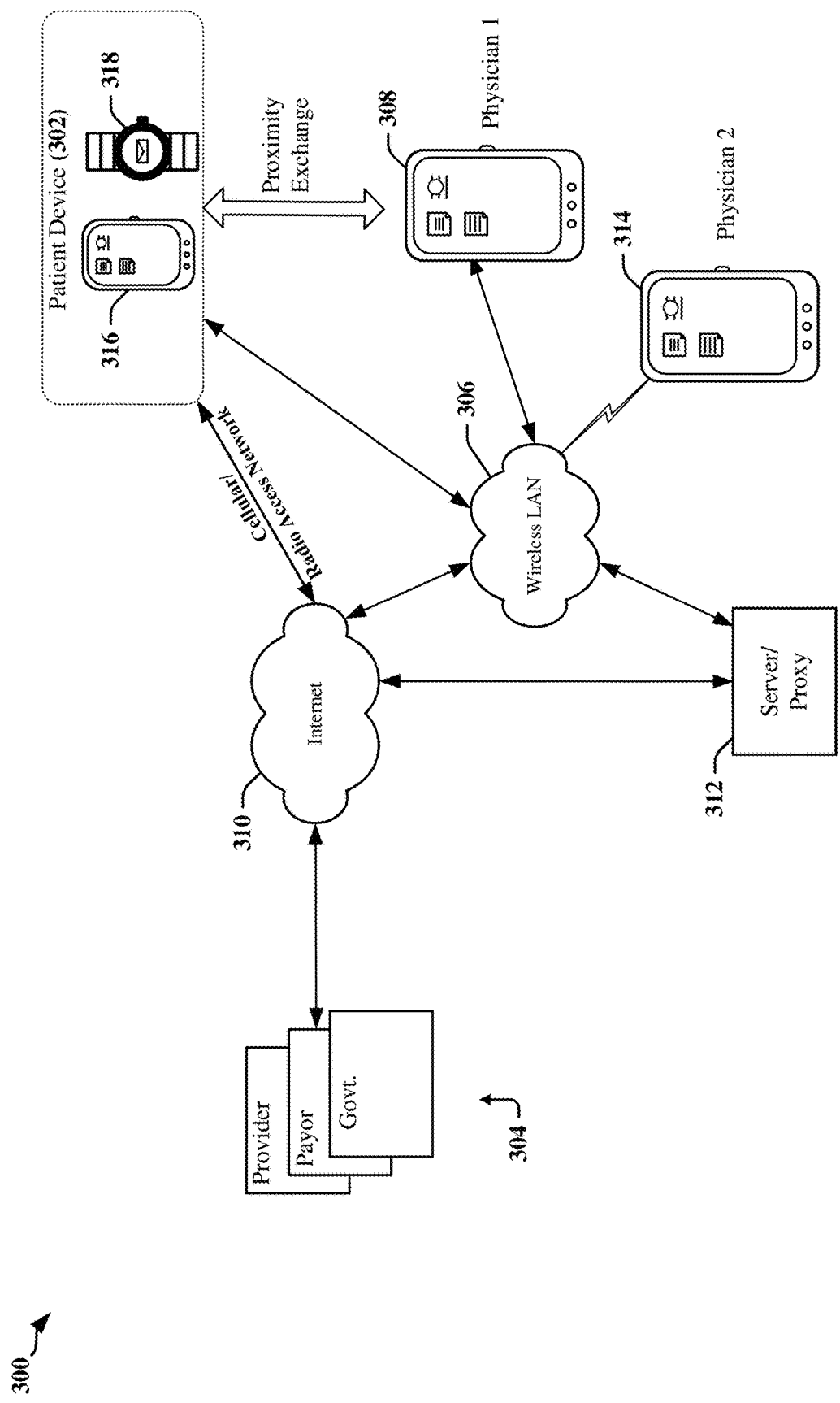
FIG. 3 illustrates flow of electronic health records between a patient and physicians in accordance with certain aspects described herein.

FIG. 3 is a diagram 300 depicting an example of a network architecture that can support the various data flows involved in transactions related to the transfer of EHRs in accordance with certain aspects disclosed herein. In a first scenario, a record owner may use a personal portable computing device (patient device 302) to directly transfer, or push, a combined record to a first provider device 308. For example, a patient visiting a physician's office may wish to provide updated records to the attending physician. In one example, the patient may initiate an agent or other application on a patient device 302 to perform the transfer, where the patient device may be a smartphone 316 and/or a smartwatch 318. The user may be required to provide identifying information, such as a username, a password, an answer to a challenge question and/or the user may be required to provide biometric information, such as a fingerprint, iris scan or submit to facial recognition process or the like. The user may typically select which records should be provided to the physician.

Upon authentication, the agent may determine if a single or combined record is maintained on the patient device 302 and whether such record is current. The agent may request records from one or more healthcare providers, insurers, government agency, public payer or other source of EHR information (shown generally at 304). Having combined or updated the individual record or records, the agent may cause the patient device 302 to push a single record or a set of combined records to the physician device 308 for immediate display. An application or agent on the physician device 308 may be manually initiated to receive the pushed information. In some embodiments, the physician device 308 may be adapted to respond to the push by opening an application or agent to receive or display the records upon receipt of a request for connection from patient device 302.

In certain embodiments, the physician may update records or retrieve other records on the physician device 308 and cause the updated or other records to be transmitted to the patient device 302. The patient device 302 may then provide the new or updated records to one or more of the EHR systems 304 or to another provider's computing device. In some embodiments, the physician may provide medical information to the patient device 302. For example, the physician may receive an X-Ray image on device 308 and may transfer the image to the patient device 302. In another example, the physician may cause device 308 to transmit information to the patient device that provides access to instructional or educational information to the patient device 302, including information on medications, dosage regimens and general information, such as educational information related to a medical condition.

The patient device 302 and the physician device 308 may communicate using any available network or communication method, including WiFi, cellular communications, Bluetooth, IEEE 802.15 (ZigBee), and other short range wireless communications. In certain embodiments, communication between devices 302 and 308 may be restricted to the use of short range communications methods to enhance security. For example, the use of a Bluetooth link between physician device 308 and patient device 302 may limit communications range to a single room, allowing both the physician and patient to verify that communication is properly established between devices 302 and 308 and to ensure that the patient's privacy can be better protected. In certain embodiments, a patient may wish to transfer records to a physician who is not physically present using a wireless LAN 306 located in a medical facility and/or through the Internet 310 where the physician and patient are geographically remote from one another. In such cases, the patient and physician may establish a video conference connection to verify identities and to confirm that communication is properly established between the respective devices 302 and 308.

In a second scenario depicted in FIG. 3, a proxy server 312 may act as a proxy between patient device 302 and a second physician device 314. As described for the first scenario, the patient may initiate a records transfer using the patient device 302. In certain embodiments, the proxy server 312 may provide one or more services, including user identification and authentication services as well as record aggregation services when the patient device 302 is not configured or adaptable to perform such functions. For example, a record owner may provide an electronic credential 218 (see FIG. 2) to a general-purpose computing device 216, whereby the electronic credential 218 causes the computing device 216 to transmit a request for service to the proxy server 312. In one example, the proxy server 312 may provide a web page to the computing device 216 in order to permit the patient to initiate a request that may be executed by the proxy server 312 on behalf of the patient.

In another example, the patient device 302 and the second physician 314 may be unable to communicate directly. A proxy server 312 may be configured to perform a gateway or routing function that permits exchange of information between the respective devices 302 and 314 through a wide area network (such as the Internet) or a local area network, for example. The devices 302 and 314 may be unable to establish direct Bluetooth or WiFi connections with one another due to security settings of the second physician device 314 and/or the wireless LAN 306. In one example, the intermediary server or proxy server 312 may provide a gateway function through a WiFi network (e.g., the wireless LAN 306) when the patient device 302 is connected to a different domain (e.g., a guest domain), while the second physician device 314 is connected via a secured private domain of the wireless LAN 306.

Proximity Exchanges

In certain embodiments, proximity may be defined as closeness in both place and time. A proximity exchange may occur when real-time communication of health records and/or health information occurs between the patient device 302 and the physician device 308 while the devices 302 and 308 are in physical proximity with each other and the users can identify each other by direct sight. In certain embodiments, proximity exchange may be used to communicate health records and/or health information from a patient device 302 to a physician device 308 over a local wireless network during a specific time period. In certain embodiments, proximity exchange may be used to initiate the push of health records and/or health information to the physician device 308 during a specific time period, whereby the proximity exchange is used for authentications and/or to provide information necessary for secure transmission of the health records and/or health information to the physician device 308.

The time period associated with a proximity exchange may be defined by a starting time when the communicating parties can identify each other by direct sight, either on a physical line-of-sight or by viewing each other through a video communication session. Typically, the two people exchanging information may be expected to be together in the same room during the proximity exchange. As an example, a patient with a smartphone 316 and/or a smartwatch 318 can send his health records to his doctor who is waiting with her tablet (or other physician device 308) in the same examining room. In another example, a doctor can send the patient treatment instructions at the end of the visit, and/or provide literature related to a diagnosis made by the doctor. In addition to having proximity of space (i.e. being in the same room) the patient and the doctor may also have proximity of time. Each party is expecting the communication to occur more or less immediately, for instance at the time when the physician is asking her patient about his medical history. In some embodiments, virtual identification can be made when the parties can see each other's face through a video link. In some instances, video linked devices 302, 308, and/or 314 may be adapted to perform facial recognition, iris scanning, fingerprint scanning or other biometric scanning when direct and/or indirect visual identification cannot be made by the parties. In some embodiments, visual recognition or a biometric alternative is required to permit access to the EHR information to be exchanged between the parties.

Proximity exchange can provide improved security for EHR exchanges. Proximity exchanges typically limit an EHR exchange by location and time, and an EHR exchange may be initiated by an EHR owner in the presence of recipient of the EHR exchange. Moreover, the opportunity to complete an EHR exchange may be restricted in time, such that EHR exchange must be initiated within a predefined time. An EHR exchange may be characterized as a one-time push, whereby the push cannot be repeated and each push requires separate authorization by the record owner.

Proximity Exchange Examples

Figure 4:
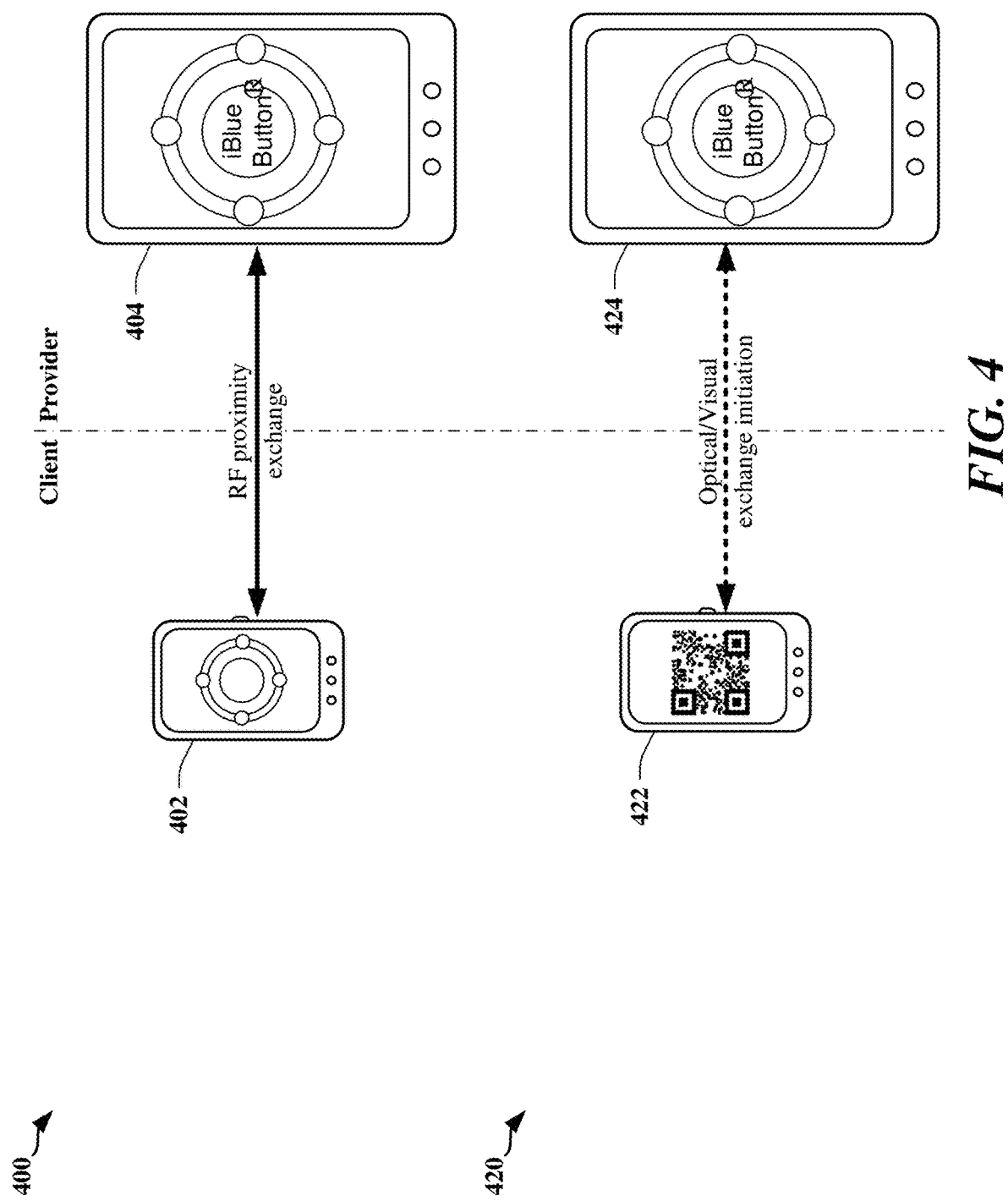
FIG. 4 illustrates a first example of proximity exchange between client and provider devices according to certain aspects described herein.

FIG. 4 includes examples 400 and 420 of proximity exchange that illustrate improved security when, for example, an EHR exchange is initiated between a patient (client) and healthcare provider. In some instances, proximity exchange may require that both parties to the exchange are in the same location and/or can visually or audibly confirm the identity of the other party. Proximity exchanges may employ limited range electronic communications, such as Bluetooth and other short-range RF communication technologies, NFC interactions, RFID, optical communications, ad hoc connections, and so on. However, proximity exchange may also include exchanges that occur within the same building and/or wireless network segment or cell, when an affirmative identification of the parties can be made.

In one example 400, a proximity exchange is enabled when two devices 402, 404 and/or 422, 424 are in direct communication and proximately located. The client device 402 may be a smartphone, tablet, a wearable computing device, a smart watch, a health or fitness tracker, eyewear, media player, appliance, or other suitable device. The client device 402 may be equipped with an agent or other downloaded application that is configured to provide access to EHR information associated with the client. The provider device 404 may be a personal computer, notebook, smartphone, tablet, media player, or other suitable device and may be equipped with an agent or downloaded application that provides provider access to one or more systems, including a practice management system, EHR systems 202, 204, 206 (see FIG. 2), and/or other systems such as an aggregator 210. The client, having decided to push EHRs to provider device 404, may interact with the agent or application on client device 402 to authenticate patient identity and initiate transfer. EHR exchange may be performed directly by client device 402, or indirectly through a proxy or other server. The client device 402 may transmit information wirelessly to the provider device 404, whereby the information may cause the agent or application on the provider device 404 to initiate receipt and acceptance of the EHRs. Typically, the client/patient may confirm that the push is targeting the provider device 404 based on a personal interaction with the provider and/or confirmation provided through interactions between the client device 402 and the provider device 404.

In another example 420, an EHR exchange can be secured even if the client device 422 is not in communication with the provider device 424 through a networking connection. For example, both devices 422 and 424 may be independently connected to the Internet but may be unable to connect by Bluetooth or by local networks such as a WiFi network, NFC or ZigBee. In some instances, the client and/or the provider may choose not to use wireless network authentication, or may be prohibited from using wireless network authentications. In some of these examples, secure EHR exchange may be provided through the use of an authentication process employing a combination of a wired network, and an authentication process that involves a proximate exchange of information.

In the depicted example 420, an EHR exchange may be secured by optically exchanging authentication information between two devices 422 and 424. The client device 422 may be a smartphone, tablet, media player, appliance or other suitable device that is equipped with a camera or optical reader. An agent or application installed on the client 422 provides access to EHR information associated with the client. The provider device 424 may be a personal computer, notebook, smartphone, tablet, media player, or other suitable device and may be equipped with a camera or optical reader. An agent or application installed on device 424 provides provider access to one or more systems, including a practice management system, EHR systems 202, 204, 206 (see FIG. 2), and/or other systems such as an aggregator 210.

The client, having decided to push EHRs to provider device 424, may interact with the agent or application on client device 422 to authenticate patient identity and initiate transfer. In order to authenticate the parties to the EHR exchange, the client device 422 may be configured to present an optical image on a display. The provider may capture the image through a camera integral to the provider device 424 or attached to the provider device 424. The image can be decoded to retrieve an encryption key, a file location, and/or other information necessary to authenticate the provider device 424 during the EHR exchange. The provider device 424 may be configured to generate and display an encoded image that can be captured by a camera of the client device 422 and decoded with a response or acknowledgement. In some embodiments, the exchange may be initiated at the provider device 424, which may create and display an image that is captured and used by client device 422 for identification purposes and to permit EHRs to be encrypted and/or directed to the provider device 424 during the EHR exchange. Any suitable type of encoded image may be used, including a barcode such as a QRC.

Electronic Heath Records Metadata

Figure 5:
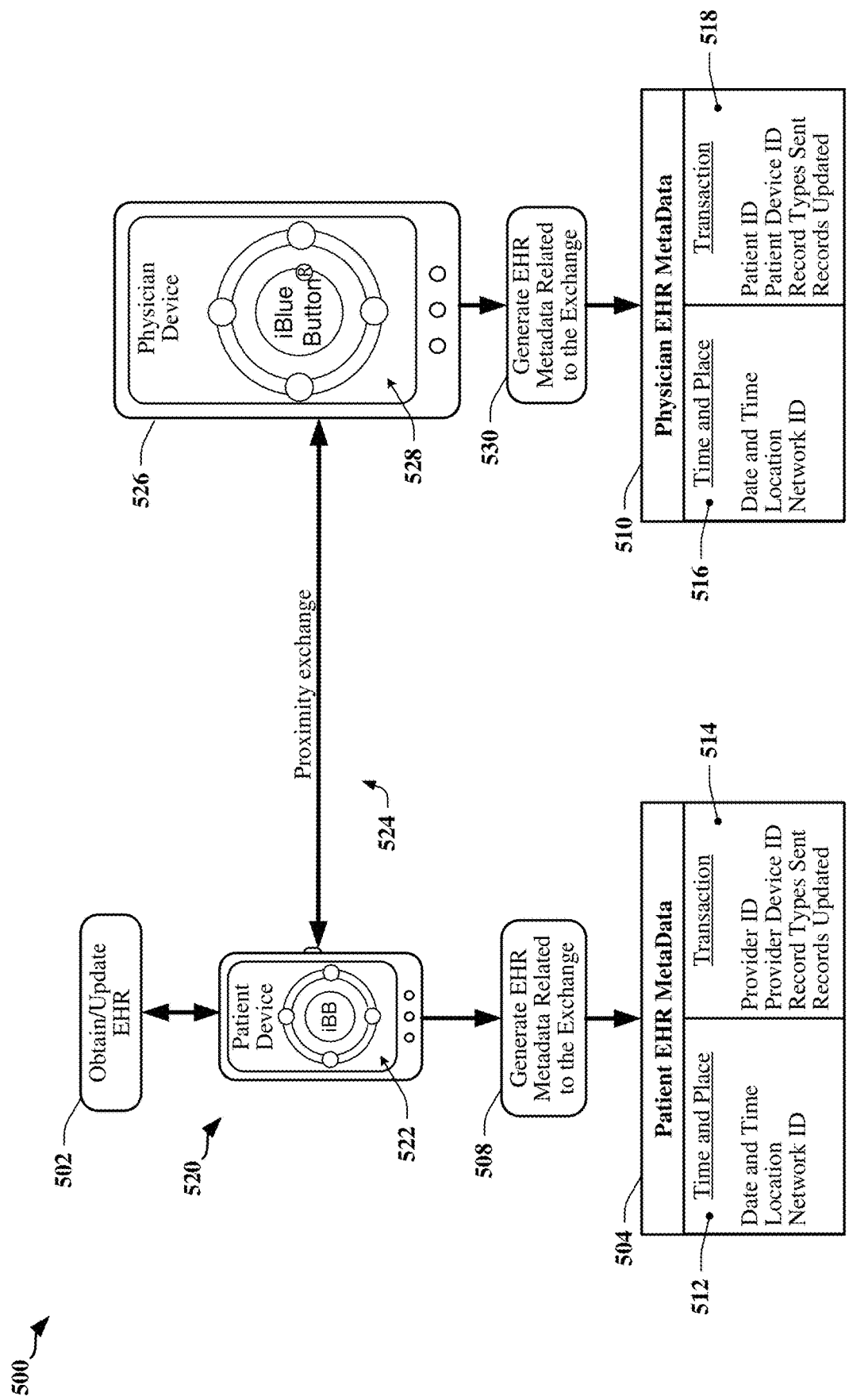
FIG. 5 illustrates certain aspects of a EHR metadata generation related to a proximity exchange in accordance with certain aspects described herein.

FIG. 5 illustrates an example of a system 500 in which EHR metadata 504 may be generated by a patient device 520 during or after an EHR proximity exchange 524 in accordance with certain aspects disclosed herein. The exchange may be initiated by a patient using a patient device 520, which may be a cellular phone, a smart phone, a session initiation protocol (SIP) phone, a laptop, a notebook, a netbook, a smartbook, a personal digital assistant (PDA), a satellite radio, a global positioning system (GPS) device, a multimedia device, a video device, a digital audio player (e.g., MP3 player), a camera, a game console, an entertainment device, a vehicle component, or a wearable computing device (e.g., a smart watch, a health or fitness tracker, eyewear, etc.).

The patient device 520 may be adapted or configured to authenticate the user (e.g., the patient) through password challenge, fingerprint identification, iris scan or other biometric measurement. The patient device 520 may maintain EHRs related to the user, where the EHRs may be maintained in encrypted storage using keys available to an authenticated user of the patient device 520. The user device may be configured or adapted to access, download and/or update 502 EHRs to be maintained on the patient device 520 from one or more sources of EHRs. The sources may include healthcare providers, payers, aggregators and/or other sources that may store EHRs of the user. Access to the sources may be enabled through a secured connection, and the sources may have shared or exchanged encryption keys and/or other information that enables the user and the source to authenticate one another. Keys and other identifying information may be maintained in a trusted environment of the user device. A trusted environment may include secure storage or a secure execution environment that has limited accessibility to ordinary applications provided on the patient device 520.

In certain embodiments, an EHR proximity exchange 524 may be enabled after a user initiates an exchange of authentication information between the patient device 520 and a provider or physician device 526. The exchange and acceptance of authentication information by the user may inherently include an authorization to the physician to access certain EHRs maintained by the user. In some examples, the EHRs are accessible to the provider or physician device 526 through the patient device 520. Access may be limited to certain records which may be determined or expected to be relevant, necessary or desirable during an interaction between a provider and a patient. The client may provide authorization to permit access to some or all relevant medical records, and the client may specify which records are relevant in the context of the interaction. Certain records may be provided for all interactions. An example of records accessible for all interactions may include "Medic-Alert" style information which identifies known medical conditions of the patient that could render the patient incapacitated, and/or that identify allergies suffered by the patient, including drug allergies or resistance or reactions to drugs that could cause distress to the patient.

In one example of an embodiment, an application such as the iBlueButton® application may be installed on the patient device 520. The application may configure the patient device 520 to provide a menu 522 on certain display screens of the patient device 520. A provider version of the iBlueButton® application (the iBlueButton Professional app or "ProApp 528") installed on a provider or physician device 526 in order to facilitate transfer of the client medical records to the ProApp 528. In some embodiments, client records are deleted after termination of the patient-provider interaction. In some instances, authorizations to transfer EHRs may be rescinded by the owner of the EHRs.

The patient device 520 may generate 508 Patient EHR metadata 504. The Patient EHR metadata 504 may include information related to activities related to healthcare services provided by one or more healthcare providers. The Patient EHR metadata 504 may include information related to quality-of-care related to the provision of the healthcare services. The Patient EHR metadata 504 may be used to determine an overall quality-of-care score.

The patient device 520 may generate Patient EHR metadata 504 after collecting contact, location, and other information associated with a proximity exchange from applications maintained by the patient device 520. Time and/or location information 512 may be determined from some combination of a clock, a GPS application and/or a network management application operating on the patient device 520. In one example, an application that manages wireless network connections (WiFi, Cellular, Bluetooth, etc.) may provide an identifier of a network access point used for the proximity exchange, where the network identifier may indicate a geographical location and identity of a healthcare provider.

The Patient EHR metadata 504 may include transaction information 514 identifying one or more transactions associated with a proximity exchange 524. Time and/or location information 516 may be determined from some combination of a clock, a GPS application and/or a network management application operating on the patient device 520. The transaction information 514 may be obtained from an EHR application such as the iBlueButton® application. The patient device 520 may provide information obtained during authentication of the healthcare provider, including information identifying the provider and/or the computing device employed by the provider to facilitate the proximity exchange 524. The transaction information 514 may include information identifying the records and/or the types of records provided to the healthcare provider. The transaction information 514 may include information identifying the records and/or the types of records updated or provided by the healthcare provider during an interaction involving a proximity exchange 524. In some implementations, the transaction information 514 may include physician recommendations and/or codes used in characterizing medical treatment. For example, the transaction information 514 may include Current Procedural Terminology (CPT®) codes defined and maintained by the American Medical Association.

In some implementations, provider EHR metadata 510 may be generated 530 on the provider or physician device 526. The provider EHR metadata 510 may include similar information regarding one or more transactions 518 with a patient and may include identification of the patient, records transferred from the patient device 520 and/or details of authorizations and consent provided during an interaction. Time and/or location information 516 may be determined from some combination of a clock, a GPS application and/or a network management application operating on the provider or physician device 526. The patient EHR metadata 504 and provider EHR metadata 510 may be compared by a third-party system to confirm details of services provided.

Figure 6:
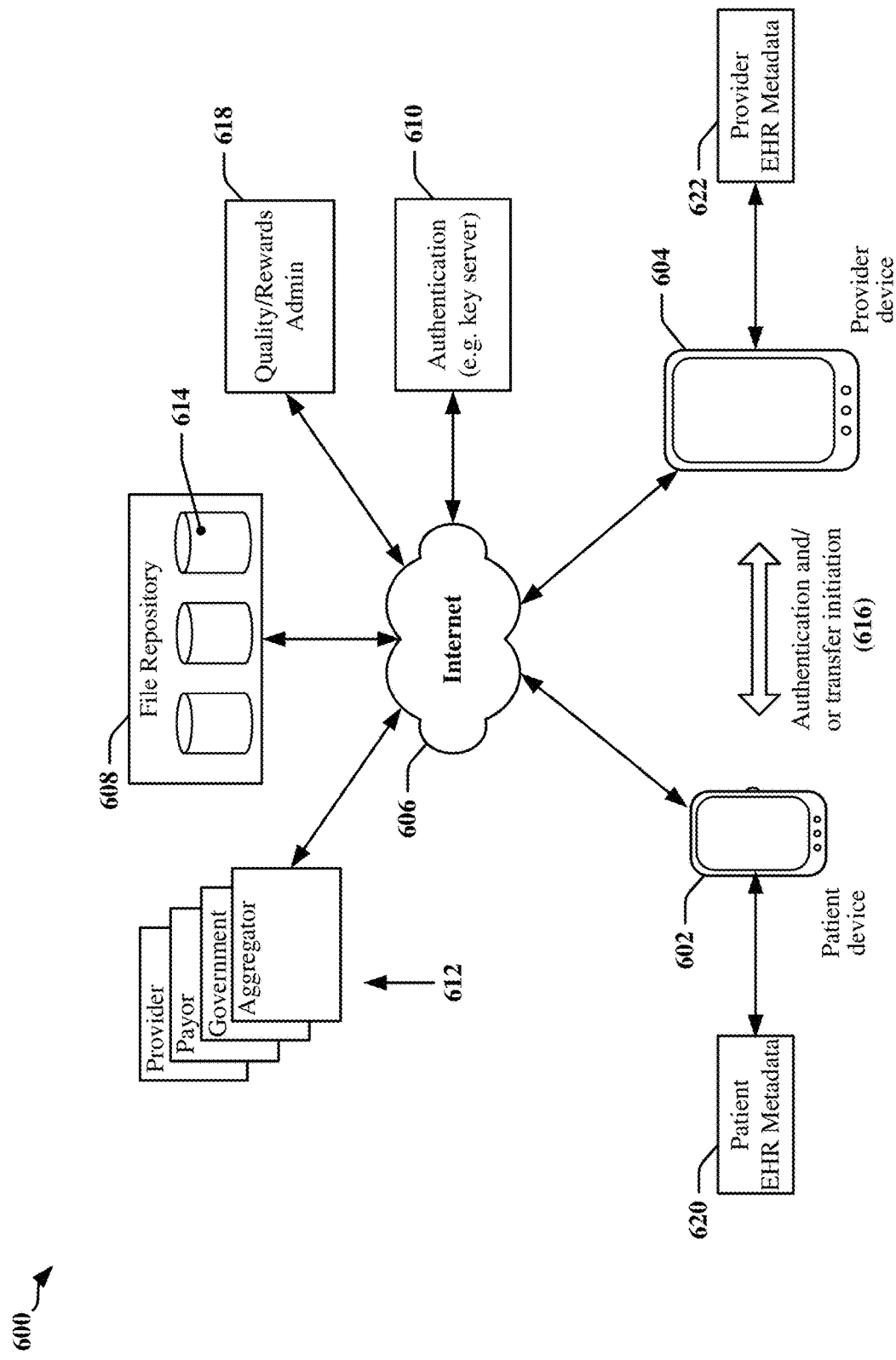
FIG. 6 illustrates an example of a system that provides secured EHR exchange and can process EHR metadata according to certain aspects described herein.

FIG. 6 illustrates an example of a system 600 that provides secured EHR exchange and can process EHR metadata 620, 622, such as the patient EHR metadata 504 and provider EHR metadata 510 illustrated in FIG. 5. Patient device 602 may identify and/or prepare a set of EHR information for transfer to the provider device 604. For example, patient device 602 may select EHR information from one or more sources to be transmitted to provider device 604. The EHR information may comprise records stored on patient device 602. The EHR information may comprise records stored in one or more EHR systems and/or aggregators 612. The type of records, sources of records, record identification and/or the subset of records for which for which consent is provided may be included in the patient EHR metadata 620.

In some instances, the patient device 602 may cause the selected EHRs to be stored in a file repository 608. File repository 608 may operate to provide a location for storage of a plurality of files and objects in a container 614 that can be uniquely identified and accessed through a network such as the Internet 606. The container 614 may be created for the duration of the EHR exchange and the container 614 may be destroyed when the contents have been forwarded to the provider device 604, or after a predetermined time. File repositories may be implemented using an Internet cloud service such as Dropbox™ or Amazon S3™. The selected EHRs may be encrypted before being stored in the container 614. The patient EHR metadata 620 may identify when a repository is used and details of the repository used for EHR transfer.

The patient device 602 and provider device 604 may exchange identifying and/or authenticating information in a proximity exchange 616 used to initiate the EHR exchange. Authentication may be supported and/or enabled by an authentication entity 610, which may be a cryptographic key generator or server, for example. The patient EHR metadata 620 and/or the provider EHR metadata 622 may record identifying and/or authenticating information. In one example, the patient EHR metadata 620 records information identifying location of an interaction with a provider, the identity of the provider, identity of a provider organization, and/or information identifying the provider device 604 and network. In another example, the provider EHR metadata 622 may record information identifying location of an interaction with a patient, the identity of the patient, and/or information identifying the patient device 602 and any intermediates, proxies or repositories 608 used in the interaction.

Typically, in-person acknowledgement is available in a proximity exchange 616, and the patient device 602 and/or the provider device 604 may enable the client and/or physician to enter information identifying the other party to an interaction. Such identifying information may be recorded in the patient EHR metadata 620, and/or in the provider EHR metadata 622. In at least some embodiments, electronic acknowledgement is made and such acknowledgements may be recorded in the patient EHR metadata 620, and/or in the provider EHR metadata 622.

In certain embodiments, cryptographic keys may be exchanged by capturing an encoded image displayed on one or more of devices 602 or 604. An asymmetric key cryptographic process may be employed to improve security of the EHR exchange. Asymmetric key cryptography systems use two separate keys which are mathematically linked. The keys may be provided by an authentication service, which can generate public and private keys for the EHR exchange. In some instances, information related to the authentication process may be recorded in the patient EHR metadata 620, and/or in the provider EHR metadata 622. Such information may include messages confirming authentication of the devices 602 or 604 and/or of the parties.

In certain embodiments, the devices 602 or 604 may be configured to record detailed information describing the EHR exchange in the patient EHR metadata 620, and/or in the provider EHR metadata 622. For example, the patient EHR metadata 620, and/or the provider EHR metadata 622 may identify components involved in the EHR exchange, affirmative acknowledgements of received information (including received EHRs), listing of content of EHR exchanges, authenticated user information, addresses of participants of EHR exchange, and/or date and time information corresponding to the EHR exchange. Information in the patient EHR metadata 620, and/or in the provider EHR metadata 622 may be obtained from transaction logs maintained by the patient device 602 and/or provider device 604.

The system 600 may include a Quality/Rewards administrator 618 that may be implemented as a standalone server or platform, or be integrated in one or more of the EHR systems and/or aggregators 612. The use of a rewards-based system can reduce errors, cost, and/or duplication of services through improved information flow initiated or enabled by a patient smartphone or other mobile communication and/or computing device. In one example, a payer may operate the Quality/Rewards administrator 618 as a tool to reduce cost or waste. In another example, a provider may operate the Quality/Rewards administrator 618 as a tool to improve efficiency and effectiveness of the healthcare services it provides.

According to one aspect, a patient or client of a payer may be rewarded for permitting EHRs to be shared with providers and EHR Metadata 620, 622 to be shared with payers, for example. Sharing EHRs with providers can reduce the risks of medical errors and instances in which redundant healthcare is provided by ensuring that a physician or other provider has a complete, relevant medical history for the patient when services are rendered. Conventionally, one in three—or fewer—physicians share records with physicians or providers from a different healthcare system. Accordingly, treatment of a patient seeking healthcare services at an urgent care facility, emergency room, specialist or at a new office may be more efficiently provided when a patient can share medical records that have been maintained or accessed through the patient device 602. The patient device may collate critical information using a healthcare application as described herein.

A patient may be incentivized to share medical records that have been maintained or accessed through the patient device 602. An insurer or other payer may make a cash award to a customer, provide a discount on rates, or provide some other valuable incentive in return for actual sharing of EHRs with a healthcare provider. In one example, the Quality/Rewards administrator 618 may collect patient EHR metadata 620 and calculate a reward based on the number of interactions with a healthcare provider that involved a sharing of EHR data. Sharing of EHR data may include uploads and downloads of EHRs that corresponds to a date of an encounter with a physician or another healthcare provider. The Quality/Rewards administrator 618 may compare the patient EHR metadata 620 with the physician EHR metadata 622 and/or with billing records to confirm that sharing of EHRs is coincident with an interaction between patient and provider. A provider may also be incentivized to participate in EHR updating through a patient device 602 during an interaction between the patient and the provider. The provider may receive some financial incentive based on the number or percentage of interactions that included a proximity exchange of EHRs.

The Quality/Rewards administrator 618 may be used in conjunction with a claims processor. The claims processor may be configured to decode medical claim data and to characterize the purpose and/or outcome of an interaction between patient and provider. The Quality/Rewards administrator 618 may provide information from the patient and/or provider that indicates whether current, relevant EHRs were provided by the patient through the patient device 602. The Quality/Rewards administrator 618 may assess whether the exchange of information assisted in preventing redundant procedures and improved efficiency. Based on the assessment, improvements in the EHR exchange process may be implemented.

The Quality/Rewards administrator 618, cooperating with the claims processor, can eliminate or reduce instances of inaccurate or fraudulent claims. For example, patient EHR metadata 620 may include information that explicitly or implicitly identifies the nature of an interaction with a healthcare provider, and an outcome of the interaction. The outcome may be recorded by the healthcare provider in EHRs that may be subsequently downloaded to the patient and/or provided to the Quality/Rewards administrator 618. The Quality/Rewards administrator 618 may request and/or periodically receive the patient EHR metadata 620. The Quality/Rewards administrator 618 may parse the patient EHR metadata 620 to identify events and interactions between patient and provider. The dates of identified events and interactions may be matched to billing entries received from a healthcare provider to ensure accuracy in reporting of the events and interactions, and to ensure that a proper and accurate accounting of procedures is available. In some instances, the Quality/Rewards administrator 618 may respond to a request from a payer to confirm occurrence of an interaction between patient and provider. The Quality/Rewards administrator 618 may search EHR data and/or previously-received patient EHR metadata 620. The Quality/Rewards administrator 618 may request that the healthcare application on the patient device 602 transfer patient EHR metadata 620 to the Quality/Rewards administrator 618. The Quality/Rewards administrator 618 may search previously received provider EHR metadata 622 and/or may request that the healthcare application on the provider device 604 or records system transfer provider EHR metadata 622 to the Quality/Rewards administrator 618. In this regard, a healthcare application on the patient device 602 may be adapted to interpret or decode ICD10 or SNOMED diagnostic codes or other medical codes such as NLM RxCui or FDA NDC medication codes provided in downloaded EHRs.

The exchange of EHRs between patient and healthcare provider typically requires consent of the patient. Consent to share EHRs during a physician visit may be inherently provided when the patient initiates a proximity exchange. In some instances, consent is affirmatively provided. A healthcare application may notify the patient that EHRs are to be transferred and may explicitly request affirmation of the desire to transfer the EHRs. In some instances, the healthcare provider may obtain consent prior to, or during an interaction between the patient and the healthcare provider. The consent may be obtained by a physician before accepting transfer of the EHRs, for example. The collection and transfer of patient EHR metadata 620 may be conditioned on prior consent provided by the patient. In some instances, the patient may enroll in a rewards program after providing consent to enable collection and transfer of patient EHR metadata 620. The collection and transfer of physician EHR metadata 622 may be conditioned on prior consent provided by the provider and/or the patient. In some instances, the provider may not have consent of the patient sufficient to generate patient-specific EHR metadata; the provider may be able to aggregate metadata for use in provider rewards program. When the patient has enrolled in a rewards program and/or the provider has obtained consent from the patient, the provider may collect and transfer provider EHR metadata 622 specific to the patient.

Other Examples of EHR and Other Information Exchanges

In certain embodiments, standardized health summaries can be made available to patients for easy download from government and private healthcare portals and to be shared with their healthcare providers. In some instances, immediate, proximate, secured exchange of health records and related health information is enabled between a patient and a physician or between two physicians. The exchange may be made in real time using mobile devices 302 and 308 (see FIG. 3). Certain embodiments of the invention enable secure and easy communication of EHR data from a patient device 302 to a physician device 308 over a local wireless network during a patient encounter with implicit or explicit patient consent. The exchange may take place in a physician's office, in an emergency room, an urgent care center, or at a hospital without a need to configure network servers and provider workstations with individual account names, addresses and security login parameters. A proximity exchange provides immediate access and secure exchange of individual health information at the time when the sender and the receiver of the information being exchanged can physically recognize each other and are reachable to each other over a network such as a wireless network.

In certain embodiments, a physician can exchange health information with a patient or with another physician using mobile devices 302, 308 and 314. The exchange can occur between two mobile phones, two tablet or other computers, or between a mobile phone and a tablet or other computer.

A patient device 302 may be adapted using an application or agent that securely stores and organizes personal health records and health information. The patient device 302 may be adapted using an application or agent that automatically accesses a patient portal account and can automatically login to retrieve current and updated patient health records. The patient device 302 may be further adapted to automatically download and combine health records from patient web portals using login and other identification and authentication maintained by the patient device 302.

In certain embodiments, the patient device 302 may be adapted to capture photographs of health documents and/or body parts using a camera in the mobile device 302. The patient device 302 may be adapted using an application or agent that accesses records created by other applications on the patient's mobile device. Proximity exchange may be used to transfer one or more health records and health information to a physician.

The patient device 302 may be adapted using an application or agent that directly receives health records, such as a visit summary, a referral note, test results, patient instructions, etc., from a physician using proximity exchange from the physician's mobile device 308.

The patient device 302 may be adapted using an application or agent that enables receipt of different types of records, including documents, photographs, audio and/or video recordings that may transferred by a physician using proximity exchange from the physician device 308 and the patient device 302 may be further configured to store and organize records exchanged to and from different physicians.

The physician device 308 may be adapted using an application or agent that can securely store and organize individual patient records and health information associated with several patients. The physician device 308 may be adapted using an application or agent that accesses records created by other applications, such as an electronic medical record (EMR) application, on the physician device 308.

The physician device 308 may be adapted using an application or agent that takes photographs of patient records and/or patient body parts using a camera of the physician device 308. The physician device 308 may be further adapted to create an audio recording, including follow-up care instructions, and to store such recordings as part of the patient's record on the physician device 308.

The physician device 308 may be adapted using an application or agent that directly receives health records from a patient, using proximity exchange from the patient's mobile device and that downloads health related information from a variety of provider, electronic medical record, health information exchange and other portals.

In some embodiments, either the patient or the doctor can initiate a proximity exchange. The initiator of the communication may push a button or otherwise activate a function of an agent or application of their respective mobile device 302 or 308. The initiator mobile device 302 or 308 may then broadcast over the wireless network an identification that may include a name that the other party can positively identify. The recipient may be notified that a request for proximity exchange has been received and may receive the name or names of the initiator. The recipient may choose between initiators detected within range of the recipient's mobile device 302 or 308 (e.g. a different physician and a different patient may be initiating an exchange in a nearby examining room). The proximity exchange may be authorized to commence when the recipient accepts the initiator.

In one example, Bluetooth and WiFi networks may be present. A mobile device may first attempt to advertise its desire to perform a proximity exchange using a WiFi Access Point (AP) if it is able to gain access to one within its wireless range. If the devices of both communication parties are able to access the same AP at the same time then the proximity exchange is performed through the AP, otherwise an attempt is made to connect them over Bluetooth. In some embodiments, Bluetooth connections are attempted first.

In certain embodiments, data is encrypted for transfer by proximity exchange. Encryption provides security that is not dependent upon on the security features of the underlying wireless network. Patient data such as health records and personal health information may be stored in encrypted form in mobile devices 302 and 308. In one example, encryption is performed using AES encryption algorithms with a secret encryption key that may be unique for the mobile device 302 or 308. The encryption keys may be generated during configuration and installation of the agent or application on the mobile device 302 or 308. Encryption keys may be based on a user password and a 64-byte random number. Encryption keys may be securely stored on the device in special secured hardware. This encryption protects both the confidentiality and the integrity of the data on the mobile devices 302 and 308.

Prior to transmission by proximity exchange, encrypted data may be first decrypted using the local cryptographic key of the sending device. The decrypted data may then be encrypted using a cryptographic key, which is known to both the sender and the receiver and which is created dynamically to exist only during the lifetime of the communication session. For example, the Diffie-Hellman algorithm may be used to create a communication session cryptographic key in such a way that only the two mobile devices 302 and 308 know the key. When encrypted data is received at the destination mobile device 308 or 302, it can be decrypted using the key associated with current proximity exchange and then re-encrypted using the local cryptographic key of the destination device before it is stored.

In certain embodiments, health records and related health information can be securely exchanged in real-time without the need for predefined network infrastructure. Proximity exchange may provide secure communication between two parties who can physically recognize each other and can communicate electronically with each other over a network.

In certain embodiments, personal identification and contact information can be exchanged between patient device 302 and physician device 308 as an option during proximity exchange. Personal identification information can include name, phone number, e-mail address, photograph, and such information may facilitate later contacts between the doctor and patient. In some embodiments, the contact information is exchanged automatically, without the requirement for each party to request it to be sent. Contact information may be automatically attached to records exchanged between the parties to enable easier filing and to enable accelerated retrieval on the respective mobile devices 302 and 308.

Figure 7:
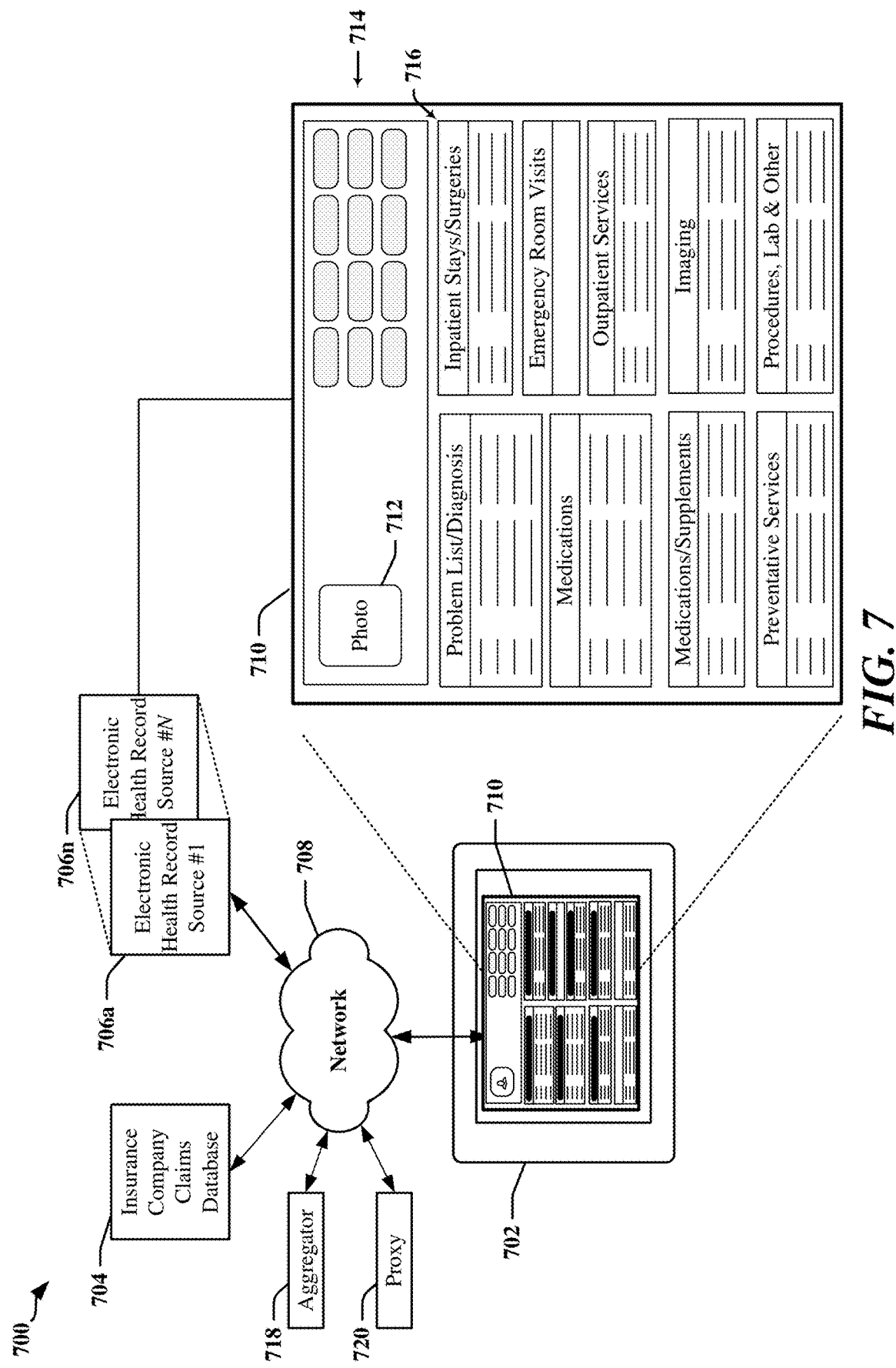
FIG. 7 illustrates an example of the delivery of medical records to users of systems deployed according to certain aspects described herein.

Record owners and providers may access the record owner EHR through a personalized portal provided on a mobile device or a conventional computing platform. Record owners may access their EHR information from a plurality of different sources and may provide one or more providers with partial or complete access to their EHR information. FIG. 7 illustrates a presentation of EHR information using a personalized portal according to certain aspects of the invention. The personalized portal may present a single display area that includes information from a plurality of sources including healthcare practitioners, insurance companies, an entity responsible for payment for services and other providers. EHR information may be combined remotely using a computer system or network server to access a plurality of EHR systems, before filtering and presenting the information to the record owner or provider. An aggregation server may reduce system complexity by providing identification, authentication, and qualification services related to the record owner and provider base as a centralized service, rather than requiring the plurality of EHR systems to maintain authentication information for the record owner and provider base. In some embodiments, a portal or agent may directly access and combine EHR information from the plurality of EHR systems.

Qualification services may filter results obtained from the plurality of EHR systems. Records received may be filtered based on certain predefined rules which may enforce government regulations. For example, certain records may not be accessible if access would cause healthcare information to be transferred between state or national jurisdictions. Records received may be filtered based on rules established by the record owner, a provider or the EHR system supplying the records. In one example, a record owner may determine a set of EHRs or a class of EHRs that should be withheld from one or more provider. The record owner may request that EHRs sent to a podiatrist should not include records related to psychiatric treatment, and vice versa.

An aggregator may format the information for display and/or may provide the information to an interface application that delivers a final format for display to the physician or other user. Interface application may be embodied in a portal or agent deployed on a record owner's computing device. Interface application may be provided as a plug-in on a network application at a provider location. Information provided by aggregator may be displayed in a web browser, a custom viewer application or in any suitable office automation application, such as a document reader or presentation tool. In certain embodiments, the display format may be specified and/or customized based on some combination of preferences and requirements of an end-user, a system administrator, a provider, payer and the record owner whose records are to be displayed. For example, the record owner may determine which fields are to be displayed and which data should be withheld. In another example, financial information is selected for display based on authorization levels set for the end-user.

In certain embodiments, the record owner is a patient who receives, or expects to receive, healthcare services in a plurality of locations from multiple healthcare providers, such as his primary care provider (physician), a physician specialist and a pharmacy. The record owner may be insured by a private or public health insurance plan. Each provider may maintain separate and distinct electronic health records for the record owner. In some embodiments, record owner is permitted access to at least a portion of the records maintained by a provider on-line when such access is for the use of the record owner. For example, a record owner may access certain records from home to check on his insurance status, medical appointments, to view prescription refills, or communicate by e-mail with attending physicians.

Certain embodiments provide a record owner-controlled, practical, flexible, direct access to the record owner's health record that is continuously available. In some embodiments, the record owner may print and/or store a summary of online records on a removable storage device when it is necessary to present EHRs to one or more providers who are not users of the electronic delivery systems described herein. It will be appreciated however, that the printed or stored records are typically static and, if not updated in a timely manner, can become outdated by the time the records are presented at the point of care. Furthermore, the saved or printed record will typically not be available at all times, including during an emergency or at the time of a routine healthcare appointment, and may not be securely stored or carried; accordingly, these stored or printed records can be subject to loss or tampering. Electronic access to EHRs may additionally resolve existing complex and ineffective patient consent management solutions, typically paper-based and single facility-based.

Consent may be provided by record owners as part of a request to deliver the record owner's EHRs. Certain embodiments provide direct access by healthcare providers to record owner records, whereby current record owner records are directly downloaded to the provider's system. The record owner may be required to provide authentication when requesting that a portion or all of the record owner's records are directly pushed to a provider system. In some embodiments, the record owner may also provide time-limited consent to permit a provider to request and access patient records directly from another service provider or from an aggregator. Consent may be provided directly by the record owner using a portal or agent, which may be implemented in a smart phone, a smart watch, a health or fitness tracker, eyewear, or other portable processing device.

Examples of Device Configuration and EHR Display

A portal or agent may be provided on a computing device. A portal may provide access to a record owner's EHR information through a browser or an application or agent that resides temporarily on the computing device. The portal may comprise an application that is downloaded and executed through a browser or loaded from a portable storage device, such as a USB drive. In one example, a USB drive may be used as a credential to identify and/or authenticate a user of the USB drive, through encryption keys, biometric information, etc., and may provide an application that enables the record owner to establish a portal on the computing device. The USB drive or another credential may be issued by his insurer, the government, or his primary healthcare provider system, etc., and may maintain record owner information such as a personal and unique identifier assigned to the record owner, a record locator address and login. The USB drive may also be configured to maintain a previously downloaded EHR document, typically in encrypted form.

The portal may comprise one or more downloadable applications and may deliver services performed by a network server. An agent may be installed or otherwise maintained by a computing device. The agent typically performs one or more functions that allow a record owner to access EHR information. The agent may identify a wireless device such as an RFID, a Bluetooth-enabled device, a WiFi connected device or another device that can be used to identify the user. The agent may be an application installed on a smart phone, tablet computer or notebook computer, whereby the record owner may use an identifier to gain access to EHR information. Identification may comprise a combination of user ID, password, challenge, biometric information such as a fingerprint, iris scan, facial scan effected by an on-board camera, and so on.

The agent or portal may be configured to perform a plurality of functions including record owner identification and authentication, access to EHRs, identification and authorization of EHRs to be pushed to a provider, aggregation of EHRs and direct push of EHRs from the record owner's personal portal to a provider's system.

In certain embodiments, a record owner may use a smart portable device that has a processor and storage. The record owner may connect a flash drive, smart card, a wirelessly connectable storage device, or the like to the computer. In one example, the record owner may present an NFC device, such as an RFID, a smart watch, a health or fitness tracker, eyewear, or smart phone that responds to or activates an NFC receiver on a provider computing workstation. The record owner may also exchange authentication information with a provider using an optical reader or camera capture barcodes displayed by user or provider, and/or to capture biometric information that automatically enables access to the EHR information. Additionally, a device-to-device communication protocol between the patient's device and a provider's portable device may be employed to automatically access and exchange electronic health records, or initiate such exchange, with the healthcare provider.

FIG. 7 is a diagram 700 illustrating an example of delivery of EHR information to a computing device 702. The computing device 702 may be operated by a healthcare provider or patient, and may comprise a tablet computer, a desktop computer, a notebook computer, or any other suitable computing device. The computing device 702 may receive and display a summary form 710 based on a patient's EHRs. The summary form is typically generated "on-the-fly" and/or on-demand. The summary form 710 may be dynamically updated to reflect activities in progress, or to add delayed information received from one or more sources of information 704, 706a-706n. The summary form 710 may be generated using information retrieved from local sources or through a network 708 which may include a local area network and/or wide area network such as the Internet. The summary form 710 may be generated from information retrieved from one or more EHR sources 706a-706n, insurance claims databases 704, or other sources. The summary form 710 may be generated from information provided by an aggregator 718 which combines information retrieved from one or more EHR sources 706a-706n, insurance claims databases 704, or other sources. The summary form 710 may be generated by an application provided in the computing device 702 or a proxy device or server 720.

The summary form 710 may be navigable, whereby a user of the computing device 702 may select certain items 712, 716 in the summary form 710 to obtain more detailed information. The summary form 710 may include controls 714 that permit a user of the computing device to initiate actions. In one example, the controls 714 may include a button or button icon that, when activated, causes the computing device 702 to retrieve additional information including contact information of the patient, providers or payers. In another example, the controls 714 may include a button or button icon that, when activated, causes the computing device 702 to present additional information related to a patient history, including a family history, allergies, immunizations and/or implanted devices. In another example, the controls 714 may include a button or button icon that, when activated, causes the computing device 702 to export or print information from the summary form 710 or other information provided in the downloaded EHRs. In another example, the controls 714 may include a button or button icon that, when activated, causes the computing device 702 to present information related to a rewards program, including terms and conditions, consent information and current rewards available to the user.

The summary form 710 may be tailored to the requirements of the user, whether an EHR holder, an insurance provider, a government agency, a physician or another healthcare provider. The summary form may be formatted for ease of viewing on any suitable platform. The summary form may be presented in a single view, window and/or screen to allow a physician or patient to access desired information in one place, with a minimum of required navigation. This single screen display can be generated on the fly and can include clinical information (e.g. in CCD/CCR format), administrative information and financial information, such as insurance eligibility information and past utilization and encounter information. The healthcare provider can typically obtain immediate access to the type, amount and location of services received by a patient, as well as out of pocket expenses incurred.

Certain processes according to certain aspects of the invention will now be described with reference to FIG. 13 and FIG. 2. For the purposes of the description, an example an embodiment of the invention used by military Veterans will be described, whereby a typical Veteran accesses healthcare at different Veterans Administration (VA) and non-VA provider sites and EHR information for the Veteran is maintained by government and non-government entities. In the example, an exchange can occur between points of care, whereby electronic health records, such as Blue Button records, can be automatically downloaded from various patient portals by a client device 214 or electronic credential 218, which has been adapted through the installation of an embedded application. Various patient portals may be accessed through client device 214, 216 and/or 218, the patient portals including "My HealtheVet" at the VA, TRI-CARE Online, and MyMedicare.gov, and other examples.

Examples of Feedback-Controlled Treatment

Figure 8:
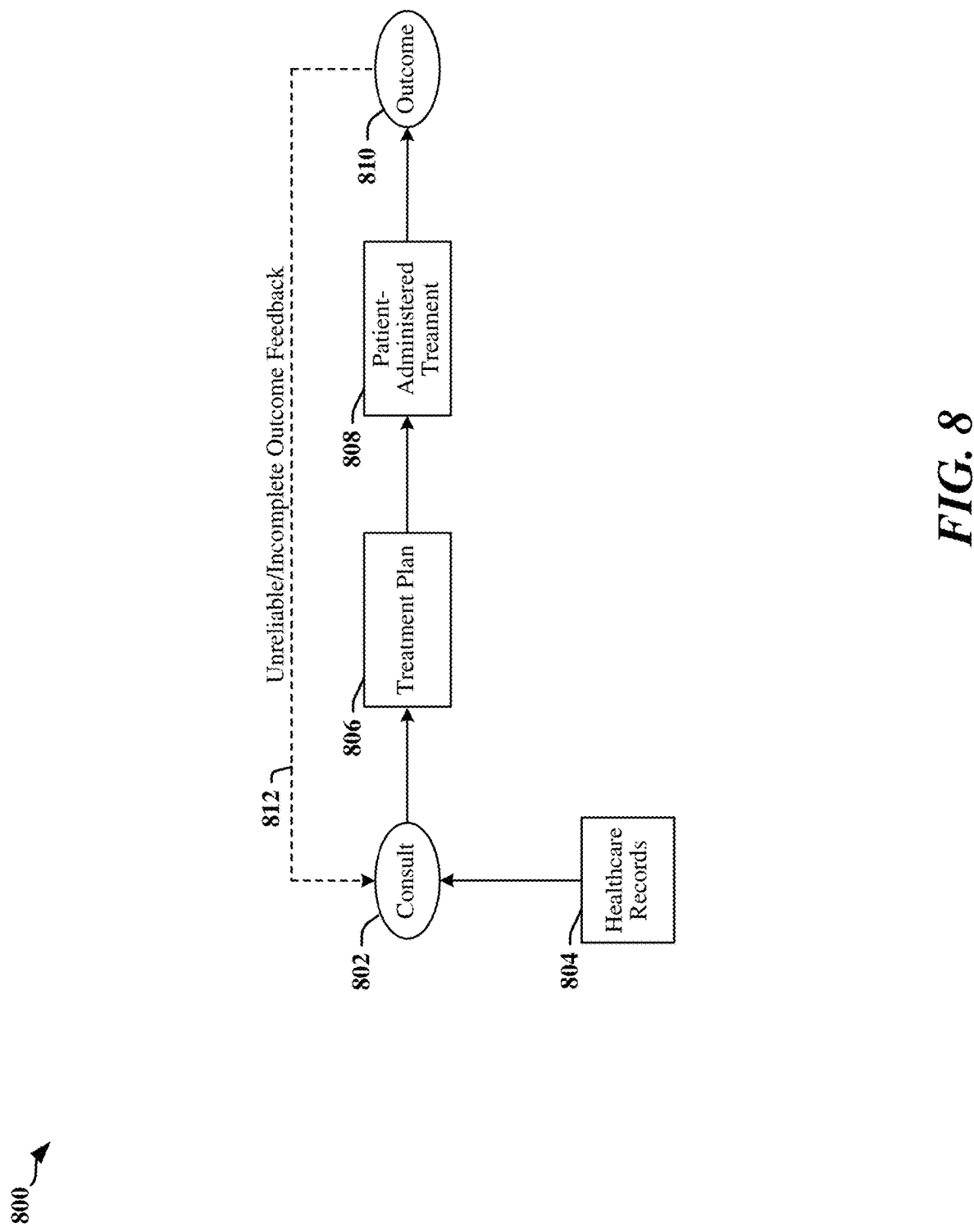
FIG. 8 illustrates an interaction between a patient and healthcare provider.

FIG. 8 illustrates a conventional approach to an interaction 800 between a patient and healthcare provider. The patient may be motivated by a medical condition to seek medical treatment. The patient may participate in a consultation 802 with a physician or other healthcare provider. The consultation 802 is typically informed or guided by patient healthcare records 804. A physician may prescribe a treatment plan 806 during or after the consultation 802. The treatment plan 806 may include a drug prescription, therapy, diet, exercise and other regimens that will be controlled by the patient. After the consultation 802, the patient may control administration 808 of the treatment plan 806. At some point in time defined by the treatment plan 806, the treatment plan 806 terminates with an outcome 810 that may be satisfactory to the patient, unsatisfactory and/or according to expectations of the physician. In many instances, the physician does not receive feedback 812 regarding the outcome 810 or quality of administration 808 of the treatment plan 806. Accordingly, the conventional approach operates as an open-loop system, or a minimally-controlled system.

Figure 9:
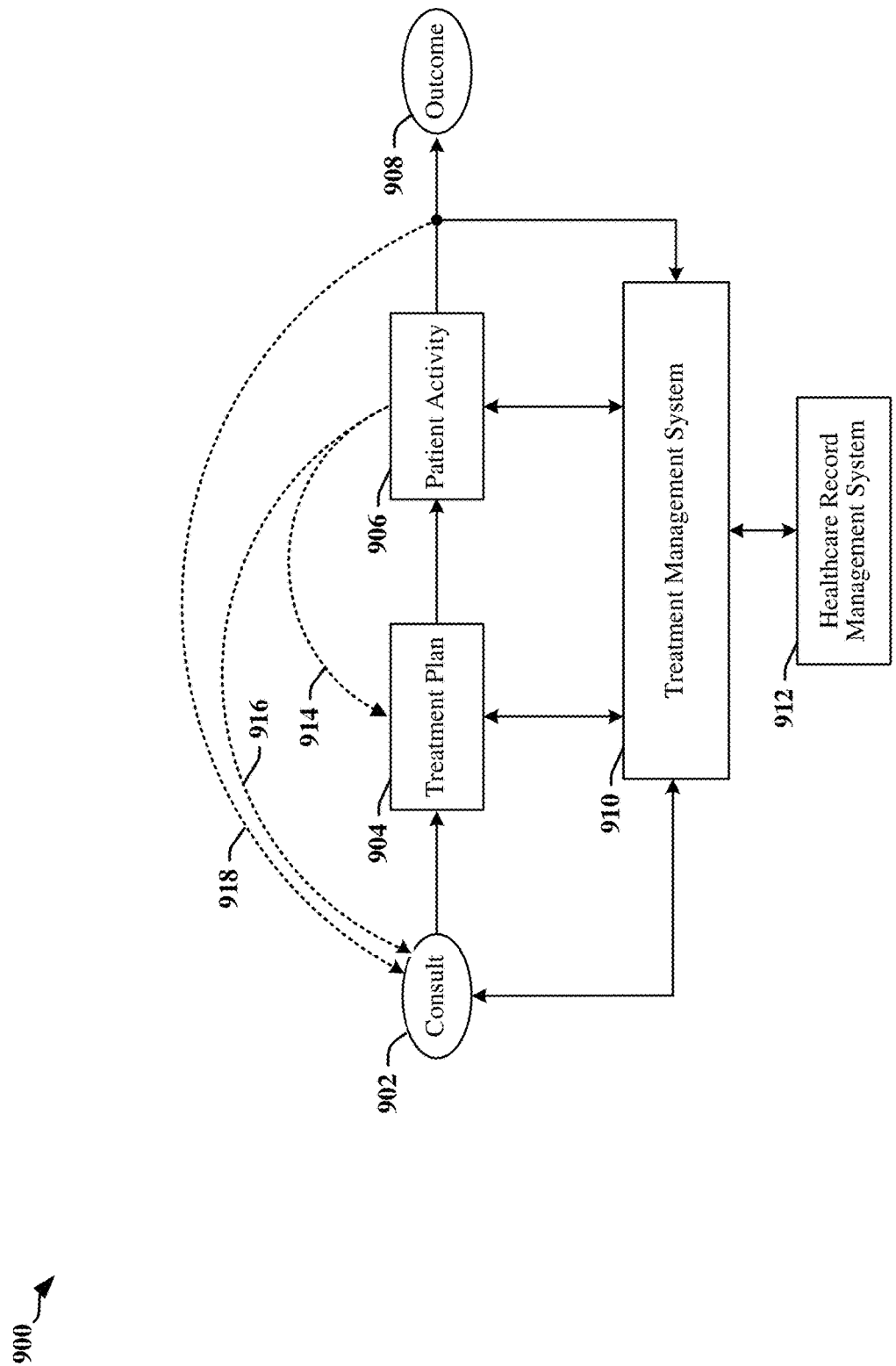
FIG. 9 illustrates a closed-loop control mechanism managing a healthcare interaction in accordance with certain aspects disclosed herein.

FIG. 9 illustrates a closed-loop control mechanism provided according to certain aspects disclosed herein that may be applied to an interaction 900 between a patient and healthcare system. The closed-loop control mechanism may leverage an integrated EHR exchange mechanism and incentive program to actively manage a treatment plan 904. The closed-loop control mechanism can effectively provide feedback loops 914, 916, 918 that enable monitoring, modification and adaptation of the treatment plan 904, prescribed patient activities 906 and expected outcomes 908. In some aspects, administration of the treatment plan 904 may be assumed by a treatment management system 910. In some examples, the treatment management system 910 may be implemented in a healthcare management system operated by a physician, physician group, hospital and/or healthcare system. In other examples, the treatment management system 910 may be implemented as a standalone system that can be configured according to the type of conditions being managed.

A patient may participate in a consultation 902 with a physician or other healthcare provider. In some instances, the patient may provide authorization for the physician to have access to healthcare records maintained by one or more EHR management systems 912. In one example, authorization may be provided through a proximity exchange as disclosed herein. A physician may prescribe a treatment plan 904 during or after the consultation 902. The treatment plan 904 may include a drug prescription, therapy, diet, exercise and other regimens that will be controlled by the patient. The physician may prescribe an application for installation on a patient mobile communication device to monitor patient activities and track incentivized activities.

In some instances, the treatment plan 904 may be generated using the treatment management system 910. In some instances, the treatment plan 904 may be developed by the physician and communicated to the treatment management system 910. The treatment plan 904 may be transmitted to a mobile communication device operated by the patient (patient device) and/or recorded in an appropriate EHR management system 912. The treatment management system 910 may establish a relationship with the patient device. The relationship between the treatment management system 910 and the patient device may be established to enable electronic communication between the treatment management system 910 and the patient device while the treatment plan 904 is in effect, where communication may be scheduled or ad hoc in nature.

In some examples, the patient device may report feedback information that can be used to assess quality-of-care. Typically, the feedback information is transmitted wirelessly from a mobile communication device. The patient device may report patient activity 906 related to the treatment plan 904. The treatment management system 910 may modify the treatment plan 904 from time to time and may update the patient device accordingly. Communication between the patient device and the treatment management system 910 provides a first type of closed-loop feedback 914, where information regarding patient activity 906 can cause adaptation of the treatment plan 904. Feedback 914 and/or the response to the feedback 914 may be recorded in an appropriate EHR management system 912.

In some examples, patient activity 906 reported by the patient device may cause the treatment management system 910 to schedule and/or initiate a request for scheduling of an additional consultation 902. The initiation or request for the additional consultation 902 may be regarded as a second type of closed-loop feedback 916. A physician may accept the request for the additional consultation 902 and/or may review feedback 916 that includes information patient activity 906, and may modify, cancel or expand the treatment plan 904 without meeting with the patient. The feedback 916 and/or the response to the feedback 916 may be recorded in an appropriate EHR management system 912.

A third type of closed-loop feedback 918 may be generated based on the patient's medical condition as reported by the patient or measured by instruments or sensors electronically coupled to the patient device. For example, measurements may be automatically relayed by the patient device from a blood pressure measurement device, a blood sugar monitor, an insulin pump (e.g., insulin dispensed), oxygen source or continuous positive airway pressure device, or other such devices, sensors or instruments. In another example, the patient may be incentivized to fastidiously report activities, symptoms and/or measurements. The treatment management system 910 may be configured to monitor and collate information received from the patient device to obtain feedback parameters. The feedback parameters may be processed to determine correction factors that can be applied to the treatment plan 904. The treatment plan 904 may be adjusted to improve the likelihood of achieving a desired or expected outcome 908. The feedback parameters and/or correction factors may be used to determine when an acceptable outcome 908 has been achieved.

The use of a closed-loop control mechanism as disclosed herein can significantly improve outcomes 908, reduce treatment periods, identify effective prescriptions and, accordingly, reduce cost of treatment. Certain aspects disclosed herein provide methodologies that facilitate the provision of accurate feedback. Primary feedback that affects the closed-loop control system may be received from patient devices (typically, smartphones) and/or physician computing systems, including desktop, laptop, tablet computers and smartphones. Secondary feedback may be provided in response to the primary feedback to incentivize or otherwise encourage the physician and/or patient to provide timely and accurate information as primary feedback. In some instances, a patient device may be configured to automatically gather information detailing patient activities and measurements generated by medical sensors or instruments. The patient device may issue alerts to the patient, where the alerts may request entry of information by the patient, and where the entered information may serve as primary or secondary feedback. The patient device may be configured to generate reminders and alarms that continue to prompt the user until information is entered.

In some embodiments, the implementation of a treatment plan 904 may be managed or controlled by a physician, a patient, the treatment management system 910, or some combination of physician, patient and treatment management system 910. Control and management of the treatment plan 904 may be facilitated by timely communication of pertinent feedback. The quality and timeliness of feedback may be improved by providing incentives to physicians and/or patients, where the incentives are earned based on feedback.

In some implementations, feedback may be prompted or triggered by an application installed on a patient's mobile device that causes the mobile device to alert patients with personalized and specific notifications related to the quality-of-care for specific medical conditions to be communicated to physicians. The notifications may relate to actions required by the physician to meet and report payer-defined quality-of-care indicators in order for the physicians to receive value-based incentive payments. In some instances, personalized and specific notifications can be generated by software, applications or another circuit or module located in the patient's mobile device. In some instances, personalized and specific notifications can be generated by applications executed in a computing cloud and communicated to the patient electronically through the patient's mobile device. Specific notifications may relate to one or more quality-of-care indicators and may be provided to prompt the patient to take a specific action to best manage a medical condition or prescribed treatment. The specific notifications may prompt the patient to communicate with a healthcare provider in order to convey the quality-of-care recommended action to be taken, to confirm that such action has been taken, and/or to communicate with the physician when the specific treatment or treatment goal has taken place or has been achieved, such that the healthcare provider can report on the recommended quality-of-care action, actual quality-of-care action taken by the physician, and/or achievement of specific quality-of-care criteria or outcomes required to obtain earned incentive payments.

According to certain aspects, a patient can be automatically alerted of a medical action his physician needs to take, if not already taken. The patient may be prompted to talk to the physician about the action. In one example, an application in a patient device (e.g., a mobile phone, instrument, sensor, etc.) notices that a diagnostic of Atrial Fibrillation has been entered or detected. A quality-of-care notification alerts the patient to need for prescription of certain medications. The quality-of-care notification may advise the patient to communicate that a physician, who may be identified by the quality-of-care notification. In some instances, the quality-of-care notification may prompt the patient to forward the quality-of-care notification or a related quality-of-care notification to the physician. In some instances, the quality-of-care notification may cause the patient device to automatically forward the quality-of-care notification or a related quality-of-care notification to the physician.

Figure 10:
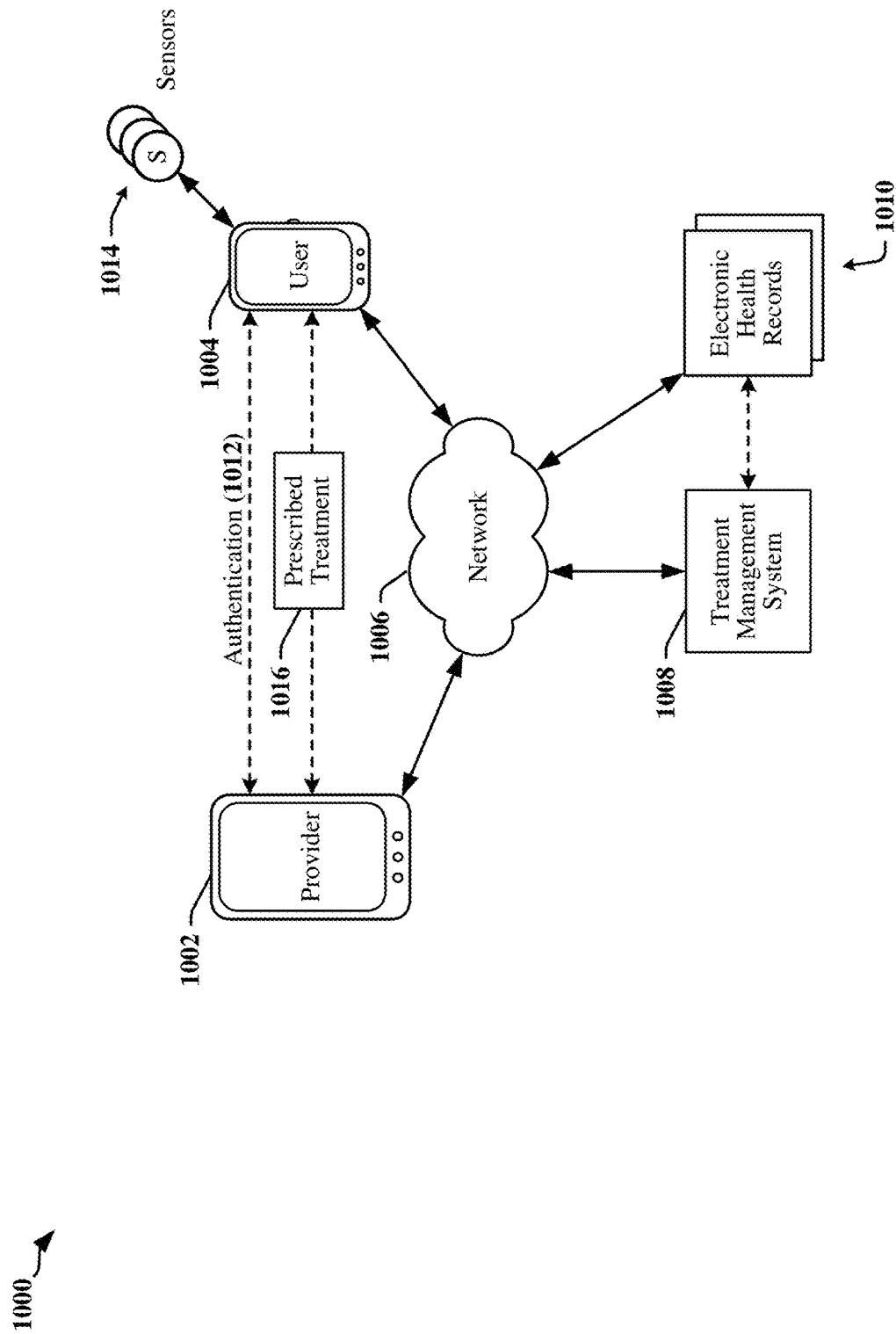
FIG. 10 illustrates a system adapted to implement a closed-loop control mechanism provided according to certain aspects disclosed herein.

FIG. 10 illustrates a system 1000 that may be adapted to implement a closed-loop control mechanism provided according to certain aspects disclosed herein. A physician or other healthcare provider may employ a physician or provider device 1002 to interact with a patient device 1004 associated with or operated by a patient during a consultation 902 (see FIG. 9). In some examples, the provider and patient may establish a connection between respective devices 1002, 1004 using an authentication process 1012 that may include or result in a proximity exchange of healthcare records in accordance with certain aspects disclosed herein. The healthcare records may be obtained from one or more electronic healthcare records management systems 1010 that are accessible by records owners or authorized users through a network 1006. The consultation 902 may be facilitated, monitored or documented using a treatment management system 1008 coupled to the physician or provider device 1002, the patient device 1004 and/or electronic healthcare records management systems 1010.

In the course of the consultation 902, or thereafter, a treatment plan may be prescribed by the physician. The prescribed treatment 1016 may be provided to the patient device 1004 directly or through the network and/or through the operation of the treatment management system 1008. The patient device 1004 may be adapted to manage execution of the prescribed treatment 1016. The patient device 1004 may communicate with the treatment management system 1008, relaying feedback information related to the prescribed treatment 1016 and/or receiving updated treatment plans. The feedback information may be derived from one or more sensors or instruments 1014 coupled to, or controlled by the patient device 1004. The feedback information may include reports of activity and other observations entered by the patient through the patient device 1004. Feedback information may be provided by a healthcare provider participating in the treatment plan or observing the effects of the treatment plan. The treatment management system 1008, the physician or provider device 1002 and/or the patient device 1004 may update the electronic healthcare records management systems 1010 during treatment.

Figure 11:
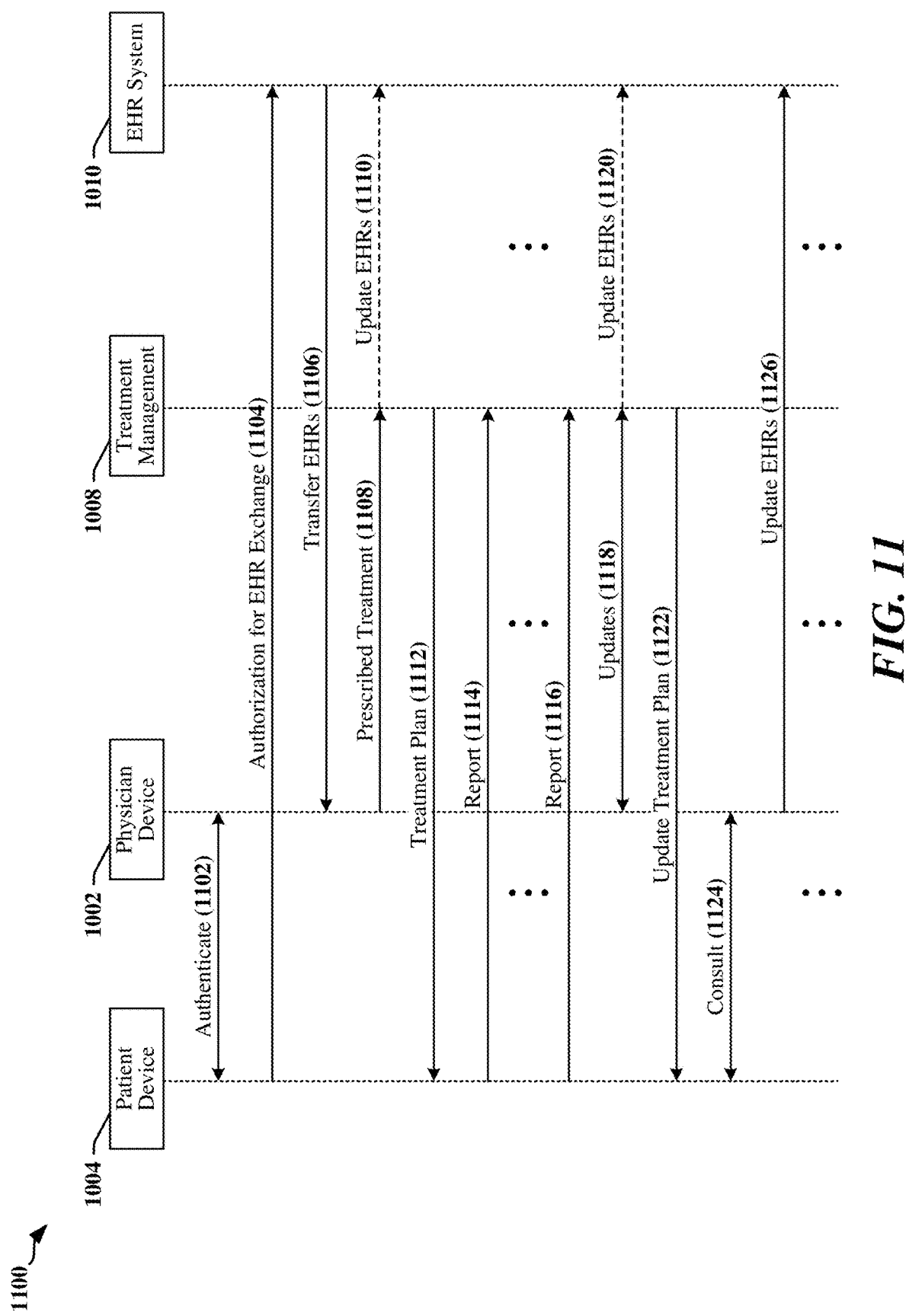
FIG. 11 illustrates a process implementing a closed-loop control mechanism provided according to certain aspects disclosed herein.

FIG. 11 illustrates a process flow 1100 that may implement a closed-loop control mechanism provided according to certain aspects disclosed herein. The process flow 1100 may relate to a process implemented using some combination of the physician or provider device 1002, the patient device 1004, the treatment management system 1008 and/or the electronic healthcare records management system 1010 illustrated in FIG. 10. The process may relate to treatment of a patient and may commence during a consultation with a physician or other healthcare provider.

The patient may authorize the physician to access healthcare records of the patient. Authorization may be provided after an authentication process 1102 that may be part of a proximity exchange between the physician or provider device 1002 and the patient device 1004. When the parties have been authenticated, the patient may prove an authorization 1104 to permit the electronic healthcare records management system 1010 to transfer records 1106 to the physician or provider device 1002. The authorization 1104 may be time limited.

In one example, the physician may prescribe treatment and may cause the physician or provider device 1002 to transmit the prescription 1108 to the treatment management system. The physician may additionally provide the prescription directly to the patient. The prescription may include an application adapted to cause the patient device to monitor prescribed treatment and provide feedback from time-to-time and/or on demand of the treatment management system 1008 or, in at least some instances, the physician or provider device 1002. The treatment management system 1008 may forward the prescription and/or a treatment plan to the electronic healthcare records management system 1010. In some implementations, the treatment management system 1008 generates the treatment plan to be transmitted to the patient device 1004. In some examples, the treatment management system 1008 transmits the treatment plan 1112 to the patient device 1004. The treatment management system 1008 may then monitor the execution of the treatment plan using feedback provided by the physician or provider device 1002 and/or the patient device 1004.

The patient device 1004 may transmit reports 1114, 1116 to the treatment management system 1008. The reports may include alerts, information about events related to the treatment plan, information obtained from sensors and/or instruments, patient-generated reports and other information related to the treatment plan. The physician or provider device 1002 may exchange updates 1118 with the treatment management system 1008. The updates 1118 may include information received directly by the physician and/or entered on, or provided to the physician or provider device 1002. The updates 1118 may include relays of information received by the treatment management system 1008 from the patient device 1004. The updates 1118 may include results generated when the treatment management system 1008 processes feedback.

The treatment management system 1008 may process feedback using an algorithm that analyzes the feedback with respect to the treatment plan and expected outcome. The algorithm may be adapted to generate suggestions, alerts and/or modifications in order to improve or modify the course of treatment. The treatment management system 1008 may update the treatment plan 1122 based on the results of processing. In one example, the treatment management system 1008 may prompt the patient to call the physician. In another example, the treatment management system 1008 may provide an analysis to the physician in order that the physician can call or meet the patient to review status. In another example, the treatment management system 1008 may prompt the physician and/or the patient to schedule 1124 a further consultation.

The treatment management system 1008 may cause the electronic healthcare records management system 1010 to be updated 1120, 1126 to reflect patient generated reports 1114, 1116, physician updates 1118, analysis of feedback, updated treatment plans and/or information arising from further consultation 1124.

Examples of Incentives Using Patient-Facing Mobile Technology

Certain aspects of the present disclosure can help solve the lack of inclusion of patient-generated data and the lack of communication between healthcare providers and their patients for physicians to optimally report on quality-of-care indicators in conventional systems. Quality-of-care indicators may be used to drive incentive payments to healthcare providers based on the care provided to their patients. Using patient-facing computer applications, which may be operated on the patient's mobile device or with virtual assistants for example, individualized and specific healthcare care notifications can be generated to guide patients in order to assist them receive effective and high-quality care. The patient-facing computer applications may enable patients to communicate with their physicians in order to exchange the information they need for quality-of-care reporting.

The patient-facing computing applications may be directly tied to a quality-of-care reporting system. In one example, the quality-of-care reporting system may be implemented using the system 600 illustrated in FIG. 6. In other examples, systems such as the Quality and Outcomes Framework (QOF) implemented in the United Kingdom of Great Britain and Northern Ireland (the UK), or the Medicare Access and CHIP Reauthorization Act of 2015 (MACRA) and/or Merit Based Incentive Payments System in the United States of America, for which the quality-of-care scoring and reporting can be a powerful incentive for healthcare practitioners, including general practitioners (GPs) in the UK to prescribe appropriate patient-facing computing applications to their patients.

In one example involving QOF, a practitioner may prescribe the Humetrix SOS QR® mobile platform for emergency care to be installed in order to, inter alia, facilitate issuance of notifications for the patients/users. The Humetrix SOS QR® mobile platform includes an embedded analytics system and algorithm. The Humetrix SOS QR® mobile platform may be selected and/or configured based on one or more QOF specific conditions entered by the user when creating their emergency record. The Humetrix SOS QR® mobile platform may alert the patient to take some QOF-specific action, and to discuss such action with their GP as needed. The Humetrix SOS QR® mobile platform may be configured to provide notifications that are designed to guide the patient to bring QOF-related care issues to their GPs, helping them achieve optimum QOF scoring. The Humetrix SOS QR® mobile platform can provide QOF values for multiple conditions, including Atrial Fibrillation (QOF #AF007), Secondary Prevention of Coronary Disease (QOF #CHD002, CHD005, CHD007), Heart Failure (QOF #HF003, HF004), Stroke and TIA, Epilepsy, among others. In one an example, the selection of Atrial Fibrillation as a condition when a user creates his emergency record via the Humetrix SOS QR® mobile platform triggers the following notification within the app to help the GP meet his AF 007 for A Fib:

"Are you taking an anticoagulation medication?
If Yes—don't forget to include this medication on your medication list.
If NOT, did you discuss this with your GP?"

In another example involving QOF, a practitioner may prescribe the Humetrix TENSIO mobile platform for hypertension management. The analytics system built into the Humetrix TENSIO mobile platform for hypertension management can issue ongoing notifications for patients and/or users to guide them and otherwise assist them to adhere to their GP treatment plan. The Humetrix TENSIO mobile platform for hypertension management can assist GPs achieve optimum QOF scoring related to the QOF specific condition addressed by the Humetrix TENSIO mobile platform for hypertension management. Multiple QOF conditions may be addressed by the Humetrix TENSIO mobile platform for hypertension management. The Humetrix TENSIO mobile platform for hypertension management can operate as a patient and clinician tool for Hypertension management (QOF #HYP006), and also for Secondary Prevention of Coronary Disease (QOF #CHD002), Stroke and TIA (QOF #STIA003), or Diabetes (QOF #DM003). The Humetrix TENSIO mobile platform for hypertension management can notify a patient user when he achieves his blood pressure target established by his GP, with a type of notification such as:

"Congratulations! Your latest blood pressure reading indicates at healthy trend towards normal. Please alert your GP of your most recent blood pressure readings, which have met his prescribed target."

The QOF hypertension (HYP 006) 150/90 mmHg blood pressure target reporting by GPs can then be optimized by patients use of TENSIO.

Examples of Processing Circuits and Methods

Figure 12:
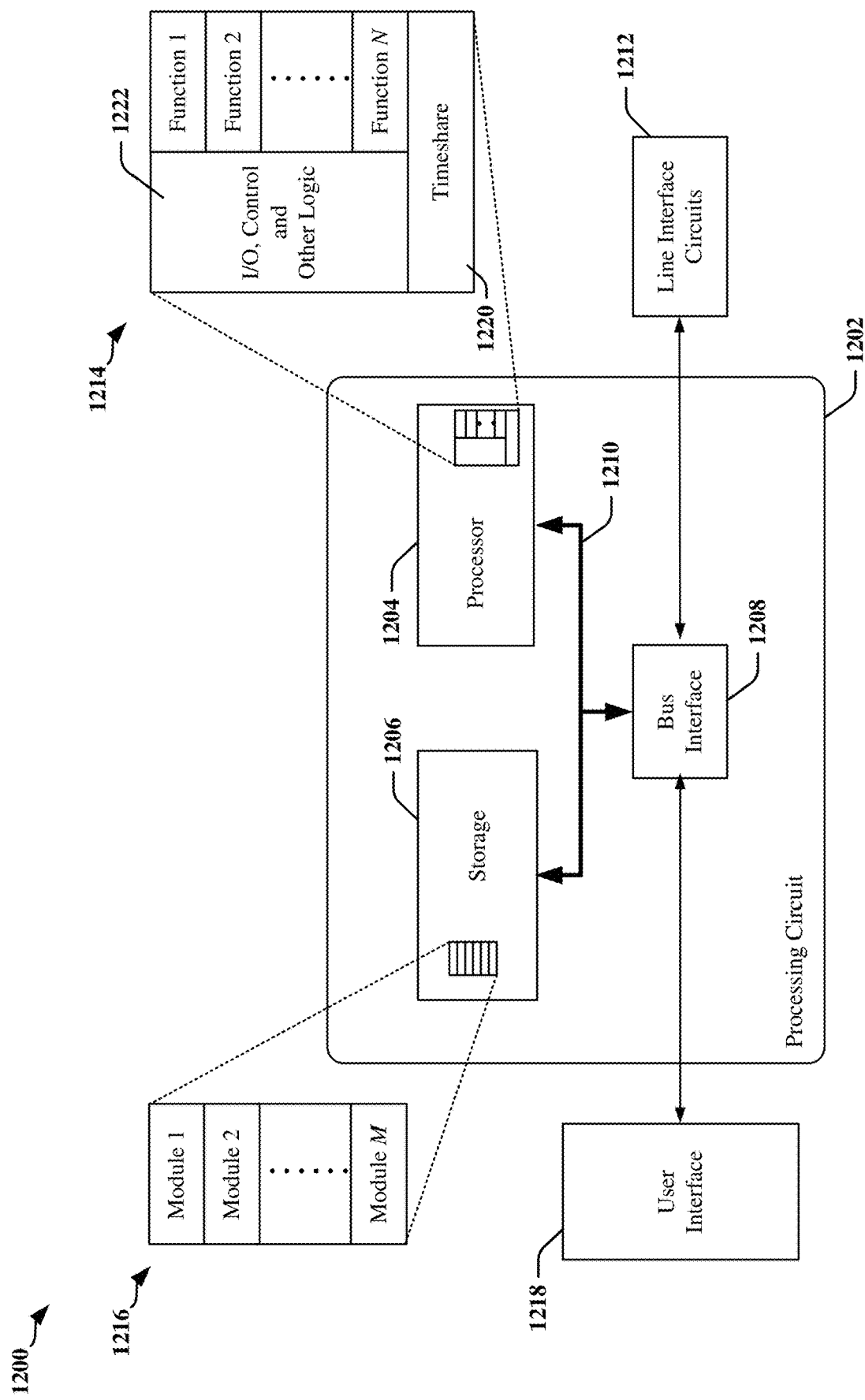
FIG. 12 is a block diagram illustrating an example of an apparatus employing a processing circuit that may be adapted according to certain aspects disclosed herein.

FIG. 12 is a conceptual diagram illustrating a simplified example of a hardware implementation for an apparatus 1200 employing a processing circuit 1202 that may be configured to perform one or more functions disclosed herein. In accordance with various aspects of the disclosure, an element, or any portion of an element, or any combination of elements as disclosed herein may be implemented using the processing circuit 1202. The processing circuit 1202 may include one or more processors 1204 that are controlled by some combination of hardware and software modules. Examples of processors 1204 include microprocessors, microcontrollers, digital signal processors (DSPs), ASICs, field programmable gate arrays (FPGAs), programmable logic devices (PLDs), state machines, sequencers, gated logic, discrete hardware circuits, and other suitable hardware configured to perform the various functionality described throughout this disclosure. The one or more processors 1204 may include specialized processors that perform specific functions, and that may be configured, augmented or controlled by one of the software modules 1216. The one or more processors 1204 may be configured through a combination of software modules 1216 loaded during initialization, and further configured by loading or unloading one or more software modules 1216 during operation.

In the illustrated example, the processing circuit 1202 may be implemented with a bus architecture, represented generally by the bus 1210. The bus 1210 may include any number of interconnecting buses and bridges depending on the specific application of the processing circuit 1202 and the overall design constraints. The bus 1210 links together various circuits including the one or more processors 1204, and storage 1206. Storage 1206 may include memory devices and mass storage devices and may be referred to herein as computer-readable media and/or processor-readable media. The bus 1210 may also link various other circuits such as timing sources, timers, peripherals, voltage regulators, and power management circuits. A bus interface 1208 may provide an interface between the bus 1210 and one or more transceivers 1212. A transceiver 1212 may be provided for each networking technology supported by the processing circuit. In some instances, multiple networking technologies may share some or all of the circuitry or processing modules found in a transceiver 1212. Each transceiver 1212 provides a means for communicating with various other apparatus over a transmission medium. Depending upon the nature of the apparatus 1200, a user interface 1218 (e.g., keypad, display, speaker, microphone, joystick) may also be provided, and may be communicatively coupled to the bus 1210 directly or through the bus interface 1208.

A processor 1204 may be responsible for managing the bus 1210 and for general processing that may include the execution of software stored in a computer-readable medium that may include the storage 1206. In this respect, the processing circuit 1202, including the processor 1204, may be used to implement any of the methods, functions and techniques disclosed herein. The storage 1206 may be used for storing data that is manipulated by the processor 1204 when executing software, and the software may be configured to implement any one of the methods disclosed herein.

One or more processors 1204 in the processing circuit 1202 may execute software. Software shall be construed broadly to mean instructions, instruction sets, code, code segments, program code, programs, subprograms, software modules, applications, software applications, software packages, routines, subroutines, objects, executables, threads of execution, procedures, functions, algorithms, etc., whether referred to as software, firmware, middleware, microcode, hardware description language, or otherwise. The software may reside in computer-readable form in the storage 1206 or in an external computer-readable medium. The external computer-readable medium and/or storage 1206 may include a non-transitory computer-readable medium. A non-transitory computer-readable medium includes, by way of example, a magnetic storage device (e.g., hard disk, floppy disk, magnetic strip), an optical disk (e.g., a compact disc (CD) or a digital versatile disc (DVD)), a smart card, a flash memory device (e.g., a "flash drive," a card, a stick, or a key drive), a random access memory (RAM), a read only memory (ROM), a programmable ROM (PROM), an erasable PROM (EPROM), an electrically erasable PROM (EEPROM), a register, a removable disk, and any other suitable medium for storing software and/or instructions that may be accessed and read by a computer. The computer-readable medium and/or storage 1206 may also include, by way of example, a carrier wave, a transmission line, and any other suitable medium for transmitting software and/or instructions that may be accessed and read by a computer. Computer-readable medium and/or the storage 1206 may reside in the processing circuit 1202, in the processor 1204, external to the processing circuit 1202, or be distributed across multiple entities including the processing circuit 1202. The computer-readable medium and/or storage 1206 may be embodied in a computer program product. By way of example, a computer program product may include a computer-readable medium in packaging materials. Those skilled in the art will recognize how best to implement the described functionality presented throughout this disclosure depending on the particular application and the overall design constraints imposed on the overall system.

The storage 1206 may maintain software maintained and/or organized in loadable code segments, modules, applications, programs, etc., which may be referred to herein as software modules 1216. Each of the software modules 1216 may include instructions and data that, when installed or loaded on the processing circuit 1202 and executed by the one or more processors 1204, contribute to a run-time image 1214 that controls the operation of the one or more processors 1204. When executed, certain instructions may cause the processing circuit 1202 to perform functions in accordance with certain methods, algorithms and processes described herein.

Some of the software modules 1216 may be loaded during initialization of the processing circuit 1202, and these software modules 1216 may configure the processing circuit 1202 to enable performance of the various functions disclosed herein. For example, some software modules 1216 may configure internal devices and/or logic circuits 1222 of the processor 1204, and may manage access to external devices such as the transceiver 1212, the bus interface 1208, the user interface 1218, timers, mathematical coprocessors, and so on. The software modules 1216 may include a control program and/or an operating system that interacts with interrupt handlers and device drivers, and that controls access to various resources provided by the processing circuit 1202. The resources may include memory, processing time, access to the transceiver 1212, the user interface 1218, and so on.

One or more processors 1204 of the processing circuit 1202 may be multifunctional, whereby some of the software modules 1216 are loaded and configured to perform different functions or different instances of the same function. The one or more processors 1204 may additionally be adapted to manage background tasks initiated in response to inputs from the user interface 1218, the transceiver 1212, and device drivers, for example. To support the performance of multiple functions, the one or more processors 1204 may be configured to provide a multitasking environment, whereby each of a plurality of functions is implemented as a set of tasks serviced by the one or more processors 1204 as needed or desired. In one example, the multitasking environment may be implemented using a timesharing program 1220 that passes control of a processor 1204 between different tasks, whereby each task returns control of the one or more processors 1204 to the timesharing program 1220 upon completion of any outstanding operations and/or in response to an input such as an interrupt. When a task has control of the one or more processors 1204, the processing circuit is effectively specialized for the purposes addressed by the function associated with the controlling task. The timesharing program 1220 may include an operating system, a main loop that transfers control on a round-robin basis, a function that allocates control of the one or more processors 1204 in accordance with a prioritization of the functions, and/or an interrupt driven main loop that responds to external events by providing control of the one or more processors 1204 to a handling function.

Figure 13:
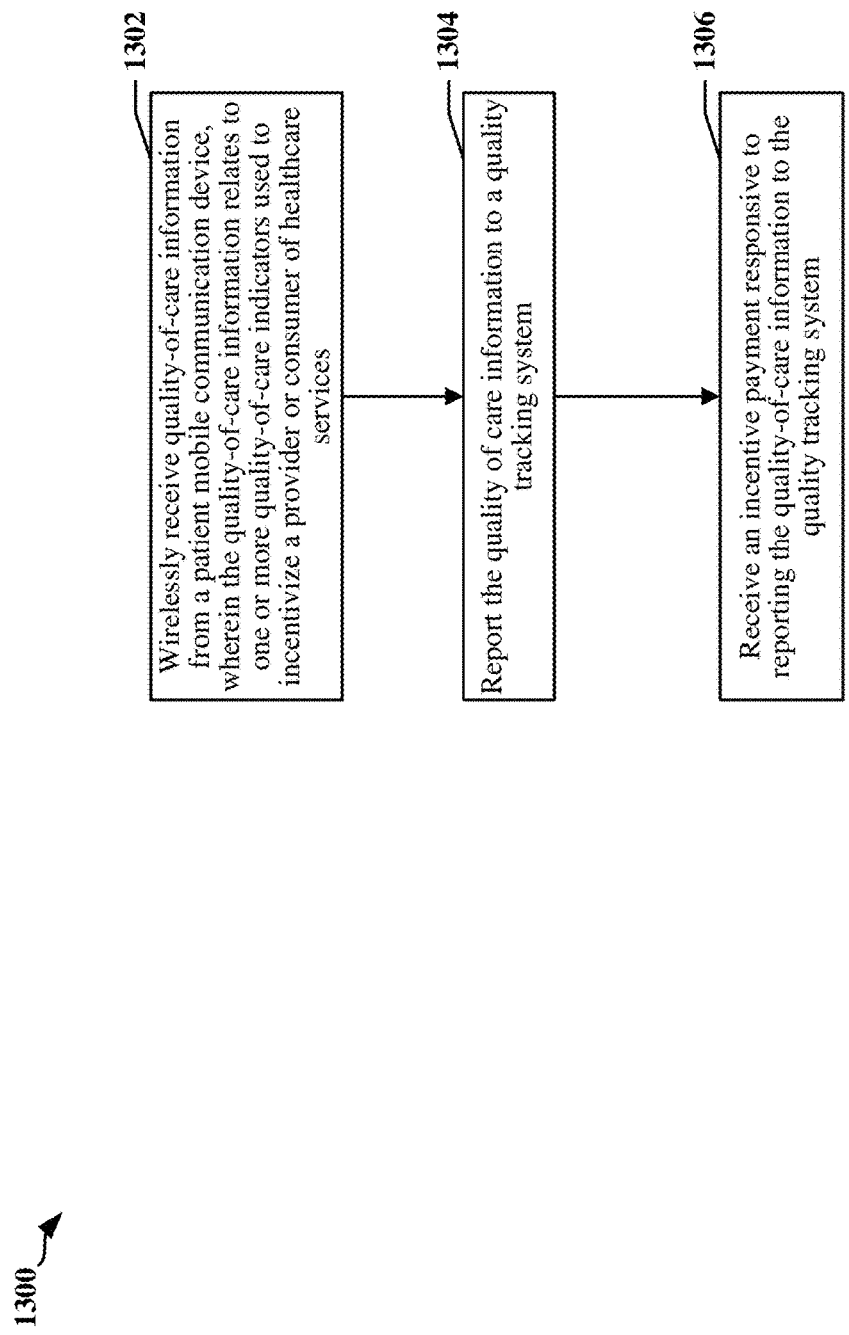
FIG. 13 includes a flowchart illustrating certain aspects of health record exchanges in accordance with certain aspects described herein.

FIG. 13 includes a flowchart 1300 that describes a method for managing healthcare services.

At block 1302, quality-of-care information may be wirelessly received from a patient mobile communication device. The quality-of-care information may relate to one or more quality-of-care indicators used to incentivize a provider or consumer of healthcare services.

At block 1304, the quality-of-care information may be reported to a quality tracking system.

At block 1306, an incentive payment may be received responsive to reporting the quality-of-care information to the quality tracking system.

In certain examples, a treatment plan may be transmitted to the patient mobile communication device, and feedback may be received from the patient mobile communication device where the feedback is related to the execution of the treatment plan. The treatment plan may be modified based on the feedback. In some instances, the feedback is provided to a management system that implements a closed-loop feedback system based on the treatment plan. The feedback may include measurements received from one or more medical sensors or instruments used to monitor a user of the patient mobile communication device. The feedback may include the quality-of-care information.

In some examples, the quality-of-care information received from the patient mobile communication device includes one or more updates of a patient medical condition. The updates of the patient medical condition may be received on a periodic basis. The quality-of-care information may include personalized notifications generated by the patient mobile communication device. The quality-of-care information may include a medical diagnosis. The quality-of-care information may relate to medications. The quality-of-care information may relate to treatment data corresponding to a user of the patient mobile communication device.

In various implementations, an application is prescribed for installation on the patient mobile communication device. The application may be operative to generate the quality-of-care information. The application may be configured to define one or more quality-of-care indicators. The patient mobile communication device may wirelessly transmit information corresponding to the one or more quality-of-care indicators. The application may be configured to alert the user of the patient mobile communication device to take a medication. The application may be configured to identify one or more conditions, medications, tests, procedures, or physiological data related to the quality-of-care indicator. The application may be configured to alert the user of the patient mobile communication device to seek medical advice when the one or more conditions occurs. The application may be configured to alert the user of the patient mobile communication device that a specific quality-of-care is recommended when the one or more conditions, medications, tests, procedures, or physiological data occurs. The application may be configured to alert the user of the patient mobile communication device of specific measures to be taken by a physician or other healthcare provider to obtain a quality-of-care indicated by the one or more conditions, medications, tests, procedures, or physiological data occurs.

In certain examples, reporting the quality-of-care information to a quality tracking system includes transferring information including a portion of the electronic healthcare records to a provider device, recording information characterizing the transfer of information to the provider device in patient metadata maintained by the patient mobile communication device, and transmitting the patient metadata to a rewards server. The rewards server may be configured to calculate a financial benefit to the user based on one or more transfers of electronic healthcare records to the healthcare provider. The rewards server may be configured to calculate the financial benefit to the user based on transmission of the updated electronic healthcare records. The updated electronic healthcare records may be decoded to identify one or more procedures performed by the healthcare provider, and to record the one or more procedures in the patient metadata.

Figure 14:
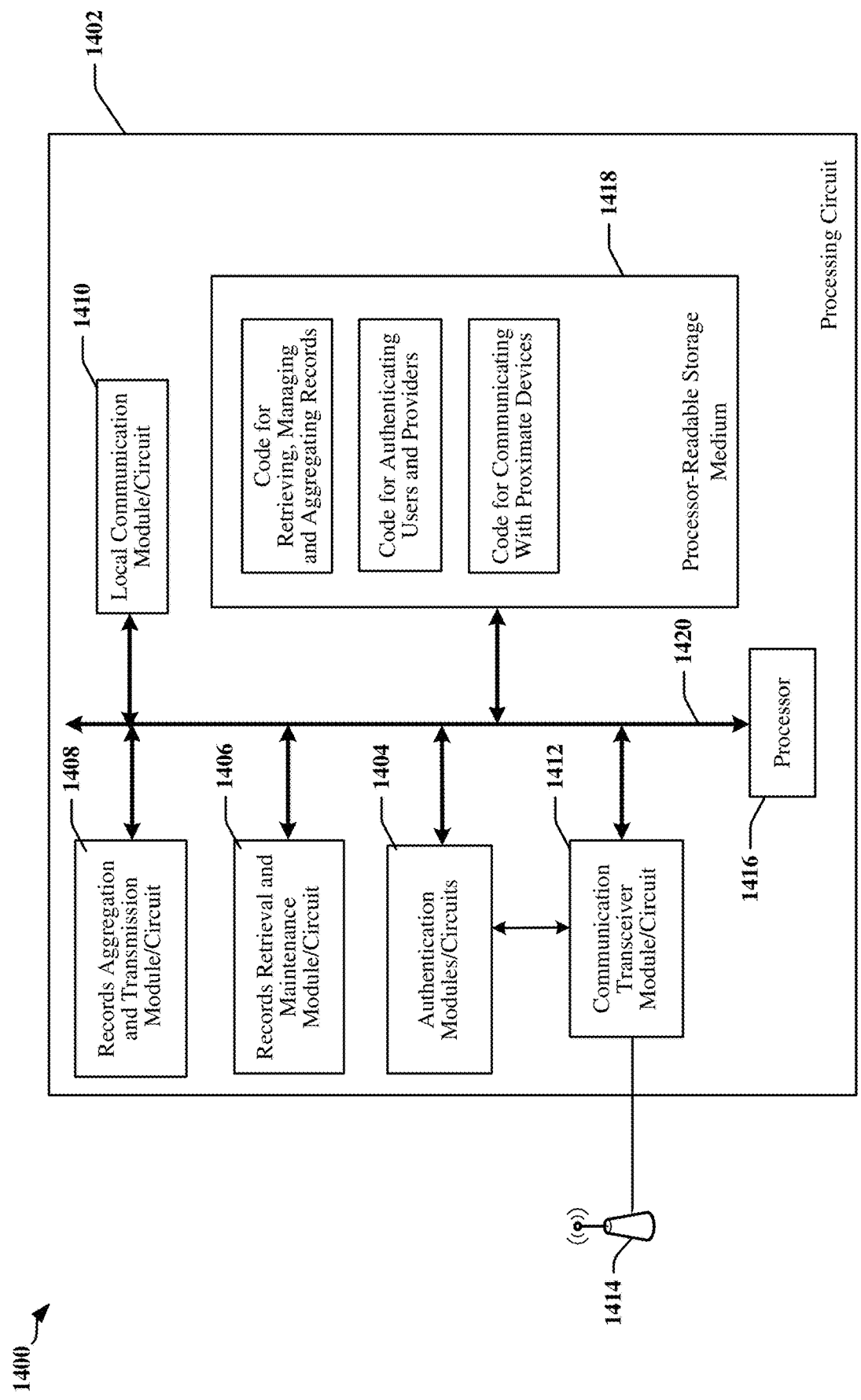
FIG. 14 illustrates a first example of a hardware implementation for an apparatus employing a processing system configured to perform certain functions according to certain aspects described herein.

FIG. 14 is a diagram illustrating a simplified example of a hardware implementation for an apparatus 1400 employing a processing circuit 1402. The processing circuit 1402 typically has a processor 1416 that may include one or more of a microprocessor, microcontroller, digital signal processor, a sequencer or a state machine. The processing circuit 1402 may be implemented with a bus architecture, represented generally by the bus 1420. The bus 1420 may include any number of interconnecting buses and bridges depending on the specific application of the processing circuit 1402 and the overall design constraints. The bus 1420 may interconnect various circuits including processors and/or hardware modules, represented by the processor 1416, the modules or circuits 1404, 1406, 1408 and 1410, a transceiver 1412 configurable to communicate wirelessly an antenna 1414 and the computer-readable storage medium 1418. The bus 1420 may also link various other circuits such as timing sources, peripherals, voltage regulators, and power management circuits, which are well known in the art, and therefore, will not be described any further.

The processor 1416 may be responsible for general processing, including the execution of software stored on the computer-readable storage medium 1418. The software, when executed by the processor 1416, may cause the processing circuit 1402 to perform certain of the functions described supra for any particular apparatus. The computer-readable storage medium 1418 may also be used for storing data that is manipulated by the processor 1416 when executing software, including data encoded in images and symbols transmitted wirelessly. The processing circuit 1402 further includes at least one of the modules 1404, 1406, 1408 and 1410. The modules 1404, 1406, 1408 and 1410 may be software modules running in the processor 1416, resident/stored in the computer-readable storage medium 1418, one or more hardware modules coupled to the processor 1416, or some combination thereof. The modules 1404, 1406, 1408 and 1410 may include microcontroller instructions, state machine configuration parameters, or some combination thereof.

Figure 15:
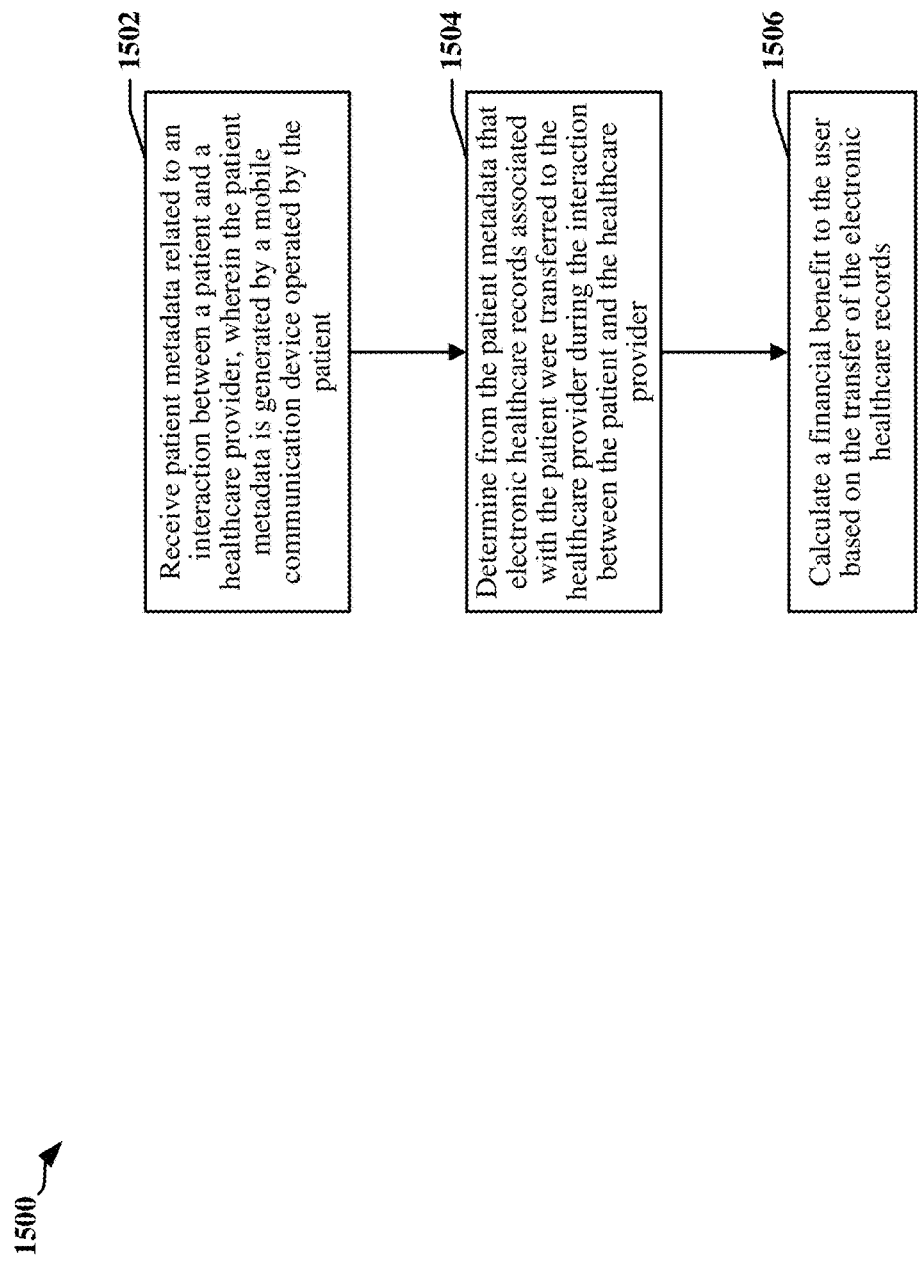
FIG. 15 includes a flowchart illustrating certain aspects of an automated health record exchange involving according to certain aspects described herein.

FIG. 15 includes a flowchart 1500 that describes a method for managing healthcare services. The method may be performed at a server.

At block 1502, the server may receive patient metadata related to an interaction between a patient and a healthcare provider. The patient metadata is generated by a mobile communication device operated by the patient.

At block 1504, the server may determine from the patient metadata that electronic healthcare records associated with the patient were transferred to the healthcare provider during the interaction between the patient and the healthcare provider.

At block 1506, the server may calculate a financial benefit to the user based on the transfer of the electronic healthcare records.

In certain examples, the patient metadata identifies that one or more updates to the electronic healthcare records were transmitted to the mobile communication device operated by the patient. The server may calculate a financial benefit to the user based on the transfer of the one or more updates. The server may decode the patient metadata to identify one or more procedures performed by the healthcare provider, and identify the procedures to a healthcare billing system. Decoding the updated electronic healthcare records may include decoding an international or national standardized health data code list for medications, diagnoses, laboratory tests, procedures, immunizations, or individual medical professions.

In certain examples, the server may receive provider metadata related to the interaction between the patient and the healthcare provider. The provider metadata may be generated by a computing device operated by the healthcare provider; and calculating a financial benefit to the healthcare provider when the provider metadata records the transfer of electronic healthcare records. The provider metadata may identify that one or more updates to the electronic healthcare records were transmitted by the healthcare provider to the mobile communication device operated by the patient. The server may calculate a financial benefit to the healthcare provider based on the transfer of the one or more updates. The server may generate a characterization of the interaction between the patient and the healthcare provider based on correspondences between the patient metadata and the provider metadata, and provide the characterization of the interaction to a healthcare billing system.

Figure 16:
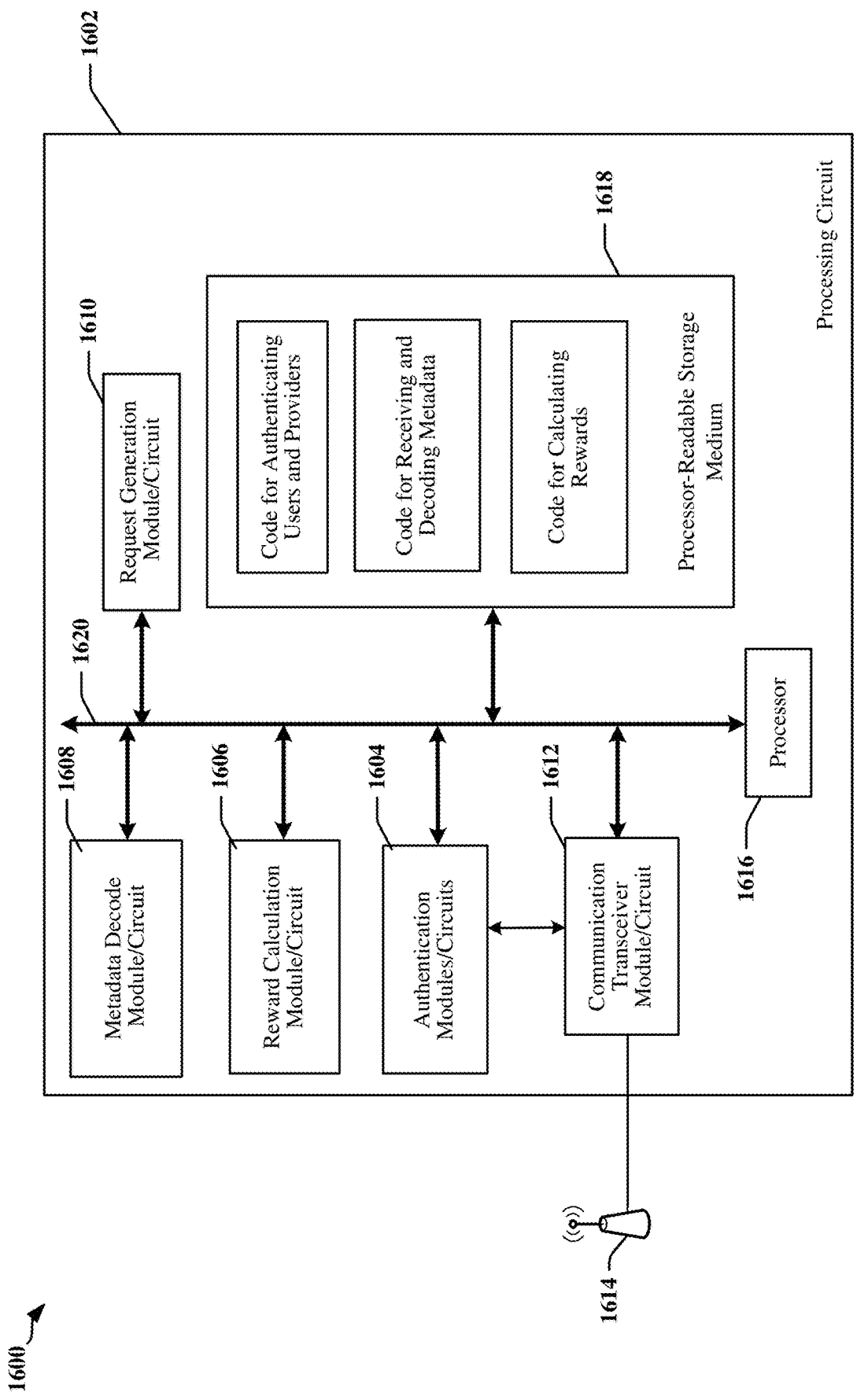
FIG. 16 illustrates a second example of a hardware implementation for an apparatus employing a processing system configured to perform certain functions according to certain aspects described herein.

FIG. 16 is a diagram illustrating a simplified example of a hardware implementation for an apparatus 1600 employing a processing circuit 1602. The processing circuit 1602 typically has a processor 1616 that may include one or more of a microprocessor, microcontroller, digital signal processor, a sequencer or a state machine. The processing circuit 1602 may be implemented with a bus architecture, represented generally by the bus 1620. The bus 1620 may include any number of interconnecting buses and bridges depending on the specific application of the processing circuit 1602 and the overall design constraints. The bus 1620 may interconnect various circuits including processors and/or hardware modules, represented by the processor 1616, the modules or circuits 1604, 1606, 1608 and 1610, a transceiver 1612 configurable to communicate wirelessly an antenna 1614 and the computer-readable storage medium 1618. The bus 1620 may also link various other circuits such as timing sources, peripherals, voltage regulators, and power management circuits, which are well known in the art, and therefore, will not be described any further.

The processor 1616 may be responsible for general processing, including the execution of software stored on the computer-readable storage medium 1618. The software, when executed by the processor 1616, may cause the processing circuit 1602 to perform certain of the functions described supra for any particular apparatus. The computer-readable storage medium 1618 may also be used for storing data that is manipulated by the processor 1616 when executing software, including data encoded in images and symbols transmitted wirelessly. The processing circuit 1602 further includes at least one of the modules 1604, 1606, 1608 and 1610. The modules 1604, 1606, 1608 and 1610 may be software modules running in the processor 1616, resident/stored in the computer-readable storage medium 1618, one or more hardware modules coupled to the processor 1616, or some combination thereof. The modules 1604, 1606, 1608 and 1610 may include microcontroller instructions, state machine configuration parameters, or some combination thereof.

It is understood that the specific order or hierarchy of steps in the processes disclosed is an illustration of exemplary approaches. Based upon design preferences, it is understood that the specific order or hierarchy of steps in the processes may be rearranged. The accompanying method claims present elements of the various steps in a sample order, and are not meant to be limited to the specific order or hierarchy presented.

Additional Descriptions of Certain Aspects of the Disclosure

Certain aspects relate to systems and methods that enable information to be securely and wirelessly exchanged under the control of a user. An image may be displayed by a mobile device for capture by a camera of the provider device. The provider device may be configured to use the cryptographic keys to access the electronic healthcare records of the user. The image may include a QRC or a barcode.

Certain aspects relate to systems and methods that enable immediate access to actionable personal health information. The personal health information may be accessed anywhere at any time. Health care quality, safety and cost-effectiveness rely on the availability of up to date and actionable personal health information at any point of care. The present invention provides a combination of innovative functionalities embedded into a mobile application running on a patient's mobile device to access, transform, aggregate and annotate personal health information so that the medical information necessary for a patient to communicate or exchange with a healthcare professional is available at all times, including offline when Internet access is not available, and in the spoken language of that health care professional to render the right care at the right time is available to any healthcare professional.

In some examples, a system may include a computing mobile device held by an individual patient running a mobile application which provide functionalities to display the individual's medical history are available offline (without Internet connection). The functionalities may include local (i.e., on a user mobile device) parsing, decoding, aggregation, classification and organization by category (such as medications, diagnoses, laboratory tests, imaging services, provider names and contact information, etc.) of the individual personal health information extracted from either health insurance claims or electronic medical records.

Certain code sets necessary for the individual data decoding are may be included or provided to the application so that the decoding and other above application functionalities are occurring in real time, and do not require an Internet access (as opposed to server based processing), so that the transformed data are available at all times. The code sets may include the various international or national standardized health data code lists for medications, diagnoses, laboratory tests, procedures, immunizations, individual medical professions, and so on. Code sets specific to geographic regions or countries may be provided or maintained, and the application allows for the display of the individual data in the language of the user's choice or the health care professional accessing that data.

According to certain aspects, individual data can be displayed in the spoken language of the healthcare professional making use of that data can be automated based on the GPS location of the individual app user or the GPS location of the health care professional accessing that data via mobile to mobile communication in various means (QR code scanning, blue tooth, Bonjour or other "Bump" technology, etc.). When translated, individual medications and immunization data are matched to the corresponding specific data where the information is being reviewed (e.g., the American medication name initially entered by an American app user, or extracted from an American medical record system will display the corresponding generic name, or brand name or both for the healthcare professional receiving or viewing that data in the country visited by the user).

According to certain aspects, the displayed individual or aggregated records are actionable by a user who can edit each data element with personal annotations; selecting his own spoken language the user can add language and region-specific health information. The displayed record data elements may be linked to various code sets so that they are searchable by the user with the link of each data element to online health information databases (e.g., Medline Plus in the U.S.A, NHS Choices in England, or Ameli.fr in France).

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for."

What is claimed is:

1. A method for managing healthcare services using a treatment management system, comprising:
    transmitting a treatment plan to a patient mobile communication device that is configured to:
        monitor at least one instrument or one or more medical sensors to obtain information related to the treatment plan, the at least one instrument or one or more medical sensors being coupled to a patient associated with the patient mobile communication device; and
        adapt the treatment plan responsive to first closed-loop feedback that includes measurements representative of blood pressure, blood sugar, dispensed insulin, oxygen or airway pressure of the patient provided to the patient mobile communication device by the one or more medical sensors or from the at least one instrument;
    receiving, at a processing system of the treatment management system, second closed-loop feedback that includes the first closed-loop feedback and responses to the first closed-loop feedback, the second closed-loop feedback being received from the patient mobile communication device;
    modifying the treatment plan at the processing system of the treatment management system in response to the second closed-loop feedback; and
    updating the patient mobile communication device with the modified treatment plan, wherein the modified treatment plan causes the patient mobile communication device to reconfigure the at least one instrument when a change in blood pressure, blood sugar, dispensed insulin, oxygen or airway pressure of the patient is detected using the measurements, and
    wherein the at least one instrument comprises an insulin pump, an oxygen source or a continuous positive airway pressure device controlled by the patient mobile communication device.

2. The method of claim 1, wherein the second closed-loop feedback includes adaptations of the treatment plan by the patient mobile communication device in response to the first closed-loop feedback.

3. The method of claim 1, wherein modifying the treatment plan at the processing system comprises:
    determining one or more correction factors to be applied to the treatment plan,
    wherein the one or more correction factors are configured to improve the likelihood of achieving an expected outcome of the treatment plan.

4. The method of claim 1, wherein the patient mobile communication device is further configured to:
    reconfigure the at least one instrument in response to changes identified by the patient mobile communication device in measurements received from the one or more medical sensors or from the at least one instrument.

5. The method of claim 4, wherein the measurements received from the one or more medical sensors or from the at least one instrument are automatically relayed by the patient mobile communication device to the processing system of the treatment management system.

6. The method of claim 1, further comprising:
    receiving one or more updates related to the medical condition of the patient through the patient mobile communication device.

7. The method of claim 6, wherein the updates related to the medical condition are automatically and periodically transmitted by the patient mobile communication device.

8. The method of claim 6, further comprising:
    receiving quality-of-care information from the patient mobile communication device,
    wherein the quality-of-care information includes personalized notifications generated by the patient mobile communication device.

9. The method of claim 8, wherein the quality-of-care information includes a medical diagnosis.

10. The method of claim 8, wherein the quality-of-care information relates to medications.

11. The method of claim 8, wherein the quality-of-care information relates to treatment data corresponding to the patient.

12. The method of claim 1, and further comprising:
    configuring the patient mobile communication device with one or more quality-of-care indicators used to generate quality-of-care information;
    wirelessly receiving information corresponding to the one or more quality-of-care indicators from the patient mobile communication device; and
    reporting the quality-of-care information to a quality tracking system.

13. The method of claim 12, further comprising:
    configuring the patient mobile communication device to alert the patient to take a medication.

14. The method of claim 12, further comprising:
    configuring the patient mobile communication device to identify one or more conditions, medications, tests, procedures, or physiological data related to the quality-of-care indicator; and configuring the patient mobile communication device to alert the patient to seek medical advice when the one or more conditions occurs.

15. The method of claim 12, further comprising:
configuring the patient mobile communication device to identify one or more conditions, medications, tests, procedures, or physiological data related to the quality-of-care indicator; and configuring the patient mobile communication device to alert the patient of specific measures to be taken by the provider to meet a quality-of-care objective related to the one or more conditions, medications, tests, procedures, or physiological data occurs.

16. The method of claim 12, wherein reporting the quality-of-care information to a quality tracking system comprises:
transferring information including electronic healthcare records to a provider device;

recording information characterizing the transfer of information to the provider device in patient metadata maintained by the patient mobile communication device; and transmitting the patient metadata to a rewards server, wherein the rewards server is configured to calculate a financial benefit to a user of the patient mobile communication device based on one or more transfers of electronic healthcare records to a healthcare provider.

17. The method of claim 16, wherein the rewards server is configured to calculate the financial benefit to the patient based on transmission of the electronic healthcare records.

18. The method of claim 16, further comprising:
decoding the electronic healthcare records to identify one or more procedures performed by the healthcare provider; and recording the one or more procedures in the patient metadata.

* * * * *